United States Patent
Einav et al.

(10) Patent No.: US 11,721,421 B2
(45) Date of Patent: Aug. 8, 2023

(54) PHARMACEUTICAL DISPENSING SYSTEM

(71) Applicant: Tech Pharmacy Services, LLC, Fort Lee, NJ (US)

(72) Inventors: Omer Einav, Kfar-Monash (IL); Doron Shabanov, Tzur-Yigal (IL); Tamir Ben David, Tel-Aviv (IL); Anthony Joseph Spero, Queensbury, NY (US); Eyal Livschitz, Givat Shmuel (IL); Thomas A. McKinney, Boonton, NJ (US)

(73) Assignee: Tech Pharmacy Services, LLC, Fort Lee, NJ (US)

( * ) Notice: Subject to any disclaimer, the term of this patent is extended or adjusted under 35 U.S.C. 154(b) by 41 days.

(21) Appl. No.: 16/558,188

(22) Filed: Sep. 2, 2019

(65) Prior Publication Data

US 2021/0065865 A1    Mar. 4, 2021

(51) Int. Cl.
*G16H 20/13* (2018.01)
*G16H 10/60* (2018.01)
*G16H 40/63* (2018.01)

(52) U.S. Cl.
CPC ........... *G16H 20/13* (2018.01); *G16H 10/60* (2018.01); *G16H 40/63* (2018.01)

(58) Field of Classification Search
CPC ......... G16H 10/60; G16H 20/13; G16H 40/63
See application file for complete search history.

(56) References Cited

U.S. PATENT DOCUMENTS

| | | | |
|---|---|---|---|
| 5,405,048 A | 4/1995 | Rogers et al. | |
| 8,700,209 B2 | 4/2014 | DiMaggio | |
| 9,268,912 B2 * | 2/2016 | Stephens | G16H 20/13 |
| 9,501,624 B2 | 11/2016 | Vishnubhatla et al. | |
| 10,025,908 B1 | 7/2018 | Orellano et al. | |
| 10,147,052 B1 | 12/2018 | Lendvay et al. | |
| 10,528,911 B1 | 1/2020 | Laster | |
| 2004/0054436 A1 | 3/2004 | Haitin et al. | |
| 2006/0253096 A1* | 11/2006 | Blakley | G07F 9/002 604/503 |
| 2007/0043469 A1 | 2/2007 | Draper | |
| 2010/0324936 A1 | 12/2010 | Vishnubhatla et al. | |
| 2013/0282401 A1 | 10/2013 | Summers | |
| 2015/0058041 A1* | 2/2015 | Ervin | G16H 70/40 705/3 |
| 2016/0085927 A1* | 3/2016 | Dettinger | G06Q 10/00 705/2 |
| 2017/0057682 A1* | 3/2017 | Chudy | B65B 43/42 |

(Continued)

FOREIGN PATENT DOCUMENTS

| | | | |
|---|---|---|---|
| WO | WO 2006/044695 | 4/2006 | |
| WO | WO-2020092756 A1 * | 5/2020 | G16H 40/63 |
| WO | WO 2022/049499 | 3/2022 | |

OTHER PUBLICATIONS

International Search Report and the Written Opinion dated Jan. 4, 2022 From the International Searching Authority Re. Application No. PCT/IB2021/057980. (13 Pages).

(Continued)

*Primary Examiner* — Shahid Merchant
*Assistant Examiner* — Steven G. S. Sanghera

(57) ABSTRACT

The present invention, in some embodiments thereof, relates to a pharmaceutical dispensing system with dynamic and automatic pharmaceutical dispensing regimes and methods thereof.

21 Claims, 12 Drawing Sheets

(56) References Cited

U.S. PATENT DOCUMENTS

| | | | |
|---|---|---|---|
| 2018/0001023 A1* | 1/2018 | Gerber | A61N 1/36185 |
| 2019/0006037 A1 | 1/2019 | Jacobs et al. | |
| 2019/0087545 A1 | 3/2019 | Sizer | |
| 2019/0206540 A1* | 7/2019 | Agassi | G06Q 10/087 |
| 2019/0244701 A1* | 8/2019 | Swenson | G16H 20/13 |
| 2021/0065866 A1 | 3/2021 | Einav et al. | |
| 2021/0158722 A1 | 5/2021 | Vyas et al. | |
| 2022/0160585 A1 | 5/2022 | Stein et al. | |
| 2022/0319686 A1 | 10/2022 | Blancke et al. | |

OTHER PUBLICATIONS

Restriction Official Action dated Sep. 6, 2022 from US Patent and Trademark Office Re. U.S. Appl. No. 17/009,953. (6 pages).
International Preliminary Report on Patentability dated Mar. 16, 2023 From the International Bureau of WIPO Re. Application No. PCT IB2021/057980. (8 Pages).
Official Action dated Feb. 21, 2023 From the US Patent and Trademark Office Re. U.S. Appl. No. 17/009,953. (40 Pages).

* cited by examiner

PHARMACEUTICAL DISPENSING SYSTEM

FIELD AND BACKGROUND OF THE INVENTION

The present invention, in some embodiments thereof, relates to a pharmaceutical dispensing system and, more particularly, but not exclusively, to a pharmaceutical dispensing system with dynamic pharmaceutical dispensing regimes.

U.S. Patent Application No. US20040054436A1 discloses "a medication dispensing system including a medicine cabinet having a plurality of compartments for containing supplies of different kinds of medications to be accessed by a healthcare attendant for preparing individual medication dosages for named patients; and a delivery device, preferably in the form of a mobile cart, having a plurality of sections for receiving medication dosages prescribed for named patients. The medicine cabinet includes a processor having a memory for storing the names of patients and their prescribed medication dosages, and a display screen for displaying the patient names and their respective prescribed medication dosages. The delivery device includes a display screen for displaying the patient names and their respective medication dosages, and a communication link with the medicine cabinet through which the cabinet processor communicates to the delivery device the patient names and their respective medication dosages."

International Patent Application Publication No. WO2006044695A1 discloses "bioactive agents are dosed by a jet dispenser using inkjet technology, such as that used in printing devices. A controller may control delivery of one or more drugs, timing of drug administration, or change drug regimens in response to a changing medical condition of a patient or information received from other nodes in a healthcare system. In a healthcare system, smart devices coupled to healthcare nodes can be in communication with the controller for controlling the administration of bioactive compositions from the jet dispenser".

SUMMARY OF THE INVENTION

According to an aspect of some embodiments of the present invention there is provided a method of managing a pharmaceutical dispensing process performed by a pharmaceutical dispensing machine, comprising:

a. receiving at least one pharmaceutical dispensing regime for at least one patient from at least one physician; said at least one pharmaceutical dispensing regime comprising at least one pharmaceutical dispensing schedule comprising at least one time of dispensing pharmaceuticals, at least one pharmaceutical and at least one pharmaceutical dispensing quantity;

b. automatically assessing a status of said patient by collecting status information of said patient at a determined time before said time of dispensing pharmaceuticals and before said pharmaceutical dispensing machine commences said pharmaceutical dispensing process;

c. automatically assessing when said status of said patient affects said at least one pharmaceutical dispensing regime;

d. automatically amending said at least one pharmaceutical dispensing regime according to said status of said patient to create at least one amended pharmaceutical dispensing regime when said status of said patient affects said at least one pharmaceutical dispensing regime;

e. dispensing by said pharmaceutical dispensing machine said at least one pharmaceutical according to said at least one amended pharmaceutical dispensing regime.

According to some embodiments of the invention, said automatically assessing a status of said patient comprises performing at least one test and said determined time before said time of dispensing is relative to the time required to receive results of said test.

According to some embodiments of the invention, said determined time before said time of dispensing is relative to the time required for the pharmaceutical dispensing machine to finish said pharmaceutical dispensing process.

According to some embodiments of the invention, automatically assessing a status of said patient comprises measuring at least one physiological parameter of said patient.

According to some embodiments of the invention, automatically assessing a status of said patient comprises measuring at least one behavioral parameter of said patient.

According to some embodiments of the invention, said automatically assessing a status of said patient comprises connecting said patient to at least one sensor.

According to some embodiments of the invention, said at least one sensor is selected from the group consisting of thermometer, weight meter, blood pressure sensor, sleep sensor, movement sensor, cardiac activity sensor, neuroactivity sensor, muscle activity sensor, breathing sensor, invasive blood test sensor, external blood test sensor, acoustical sensor, imaging sensor for detection of ear infections, imaging sensor for detection of throat infections, epileptic seizure sensor, drug level in blood assessment sensor, a swallowed sensor comprising a plurality of sensors in it and any combination thereof.

According to some embodiments of the invention, said status information comprises at least one selected from the group consisting of temperature, weight, blood pressure, sleeping patterns, movement patterns, cardiac activity, neurological activity, muscle activity, breathing patterns, blood content, acoustical data, ear infection status, throat infection status, epileptic activity, drug levels in the blood and any combination thereof.

According to some embodiments of the invention, automatically amending said at least one pharmaceutical dispensing regime further comprises notifying said at least one physician of said at least one amended pharmaceutical dispensing regime.

According to some embodiments of the invention, said determined time before said time of dispensing is from about 1 minute to about 3 hours.

According to some embodiments of the invention, said automatically assessing a status of said patient comprises sending information about said assessment status to at least one server to be analyzed by an assessment tool software.

According to some embodiments of the invention, said automatically assessing a status of said patient further comprises revising if said physician provided conditions on which said pharmaceutical dispensing regime needs to be amended according to a status of the patient close to the time of dispensing pharmaceuticals.

According to some embodiments of the invention, said automatically assessing when said status of said patient affects said at least one pharmaceutical dispensing regime comprises comparing said status information with data located in said server.

According to some embodiments of the invention, said automatically assessing when said status of said patient affects said at least one pharmaceutical dispensing regime comprises comparing said status information with historical status data content.

According to some embodiments of the invention, said automatically assessing when said status of said patient affects said at least one pharmaceutical dispensing regime comprises comparing said status information with assessment data.

According to some embodiments of the invention, said automatically assessing when said status of said patient affects said at least one pharmaceutical dispensing regime comprises comparing said status information with status information from other patients in the vicinity of said patient.

According to some embodiments of the invention, said method further comprises updating said database with data received during the managing of said pharmaceutical dispensing process.

According to an aspect of some embodiments of the present invention there is provided a method for assessing a pharmaceutical dispensing regime performed by at least one pharmaceutical dispensing machine wherein one or more processors in one or more network computers execute instructions to perform actions, comprising:
a. employing one or more assessment tool software to perform actions including:
 i. collecting status data of patient including physiological information associated with one or more physiological states of said patient; said collecting is performed before commencing a pharmaceutical dispensing process;
 ii. employing one or more classifiers to perform actions, including:
  A. classifying said status data of patient to determine one or more occurrences of one or more physiological states of said status data of said patient; and
  B. classifying assessment content to determine one or more scores that are associated with one or more physiological states included in the one or more physiological states of said patient, wherein the assessment data includes information associated with one or more physiological states of the one or more physiological states of said patient; and
 iii. providing one or more correlation values associated with the status data of patient based on historical status data content, assessment data, and scores;
 iv. employing the one or more correlation values to provide an amendment to said pharmaceutical dispensing regime, wherein the amendment includes one or more of an amendment in a pharmaceutical dispensing schedule, an amendment in a pharmaceutical dispensing quantity or an amendment in a pharmaceutical dispensing type of pharmaceutical; and
 v. instructing said pharmaceutical dispensing machine to dispense to said patient pharmaceuticals according to an amended pharmaceutical dispensing regime based on the correlation values, status data, assessment data and scores.

According to some embodiments of the invention, collecting status data includes:
a. receiving at least one physiological information related to said patient; and
b. generating the assessment data based on said at least one physiological information.

According to some embodiments of the invention, classifying the assessment data further comprises:
a. classifying physiological data provided by different sources; and
b. further determining the one or more scores based on the classification of the physiological data.

According to some embodiments of the invention, employing one or more assessment tool software to perform actions, further comprises:
a. providing real-time feedback to one or more subjects from which status data is being collected; and
b. collecting one or more responses from the one or more subjects that are associated with the real-time feedback.

According to some embodiments of the invention, further comprising updating the one or more classifiers based on the one or more correlation values.

According to some embodiments of the invention, employing one or more assessment tool software to perform actions, further comprises:
a. extracting a portion of the performance content associated with the assessment data based on the one or more scores that exceed a defined value; and
b. providing the extracted portion of the performance content and its assessment data to a classification processing engine for use as training data.

According to some embodiments of the invention, providing one or more correlation values associated with the status data, further comprises:
a. receiving a current physiological status that comprises one or more current physiological data;
b. correlating the current physiological status with at least one of historical status data content, assessment data, and scores; and
c. modifying the one or more classifiers based on the correlation of the current physiological status with said at least one of historical status data content, assessment data, and scores.

According to some embodiments of the invention, said information included in said assessment data is current physiological information related to said patient received by at least one of a patient assessment unit and a dedicated personnel's device.

According to an aspect of some embodiments of the present invention there is provided an automatic pharmaceutical dispensing assessment unit for a pharmaceutical dispensing system that performs at least one pharmaceutical dispensing process, the unit comprising:
a. at least one processor device;
b. at least one computer readable medium having computer program instructions thereon;
c. at least one communication unit in communication with:
 i. at least one server of a pharmaceutical dispensing system; and
 ii. at least one patient assessment unit;
 iii. at least one pharmaceutical dispensing machine;
wherein said at least one processor device execute said program instructions to perform actions, including:
d. receiving at least one pharmaceutical dispensing regime for at least one patient from at least one physician; said at least one pharmaceutical dispensing regime comprising at least one pharmaceutical dispensing schedule comprising at least one time of dispensing pharmaceuticals, at least one pharmaceutical and at least one pharmaceutical dispensing quantity;
e. automatically assessing a status of said patient by collecting status information of said patient by said at least one patient assessment unit at a determined time before said time of dispensing pharmaceuticals and before said pharmaceutical dispensing machine commences said pharmaceutical dispensing process;

f. automatically assessing when said status of said patient affects said at least one pharmaceutical dispensing regime;

g. automatically amending said at least one pharmaceutical dispensing regime according to said status of said patient to create at least one amended pharmaceutical dispensing regime when said status of said patient affects said at least one pharmaceutical dispensing regime;

h. dispensing by said pharmaceutical dispensing machine said at least one pharmaceutical according to said at least one amended pharmaceutical dispensing regime.

According to some embodiments of the invention, said automatic pharmaceutical dispensing assessment unit is located within said pharmaceutical dispensing machine.

According to some embodiments of the invention, said automatic pharmaceutical dispensing assessment unit is located outside said pharmaceutical dispensing machine.

According to some embodiments of the invention, said automatic pharmaceutical dispensing assessment unit is located at a remote location and in direct communication with said pharmaceutical dispensing machine.

According to some embodiments of the invention, said automatically assessing a status of said patient comprises performing at least one test and said determined time before said time of dispensing is relative to the time required to receive results of said test.

According to some embodiments of the invention, said determined time before said time of dispensing is relative to the time required for the pharmaceutical dispensing machine to finish said pharmaceutical dispensing process.

According to some embodiments of the invention, automatically assessing a status of said patient comprises measuring at least one physiological parameter of said patient.

According to some embodiments of the invention, automatically assessing a status of said patient comprises measuring at least one behavioral parameter of said patient.

According to some embodiments of the invention, said automatically assessing a status of said patient comprises connecting said patient to at least one sensor.

According to some embodiments of the invention, said at least one sensor is selected from the group consisting of thermometer, weight meter, blood pressure sensor, sleep sensor, movement sensor, cardiac activity sensor, neuro-activity sensor, muscle activity sensor, breathing sensor, invasive blood test sensor, external blood test sensor, acoustical sensor, imaging sensor for detection of ear infections, imaging sensor for detection of throat infections, epileptic seizure sensor, drug level in blood assessment sensor, a swallowed sensor comprising a plurality of sensors in it and any combination thereof.

According to some embodiments of the invention, said status information comprises at least one selected from the group consisting of temperature, weight, blood pressure, sleeping patterns, movement patterns, cardiac activity, neurological activity, muscle activity, breathing patterns, blood content, acoustical data, ear infection status, throat infection status, epileptic activity, drug levels in the blood and any combination thereof.

According to some embodiments of the invention, automatically amending said at least one pharmaceutical dispensing regime further comprises notifying said at least one physician of said at least one amended pharmaceutical dispensing regime.

According to some embodiments of the invention, said determined time before said time of dispensing is from about 1 minute to about 3 hours.

According to some embodiments of the invention, said automatically assessing a status of said patient comprises sending information about said assessment status to at least one server to be analyzed by an assessment tool software.

According to some embodiments of the invention, said automatically assessing a status of said patient further comprises revising if said physician provided conditions on which said pharmaceutical dispensing regime needs to be amended according to a status of the patient close to the time of dispensing pharmaceuticals.

According to some embodiments of the invention, said automatically assessing when said status of said patient affects said at least one pharmaceutical dispensing regime comprises comparing said status information with data located in said server.

According to some embodiments of the invention, said automatically assessing when said status of said patient affects said at least one pharmaceutical dispensing regime comprises comparing said status information with historical status data content.

According to some embodiments of the invention, said automatically assessing when said status of said patient affects said at least one pharmaceutical dispensing regime comprises comparing said status information with assessment data.

According to some embodiments of the invention, said automatically assessing when said status of said patient affects said at least one pharmaceutical dispensing regime comprises comparing said status information with status information from other patients in the vicinity of said patient.

According to some embodiments of the invention, said method further comprises updating said database with data received during the managing of said pharmaceutical dispensing process.

According to an aspect of some embodiments of the present invention there is provided a system for assessing a pharmaceutical dispensing regime to be dispensed by a pharmaceutical dispensing machine, comprising:

a. a network computer, comprising:
 i. a transceiver that communicates over the network;
 ii. a memory that stores at least instructions; and
 iii. one or more processor devices that execute instructions that perform actions, including employing one or more assessment tool software to perform actions, including:
  A. collecting status data of patient including physiological information associated with one or more physiological states of said patient; said collecting is performed before commencing a pharmaceutical dispensing process;
  B. employing one or more classifiers to perform actions, including:
   I. classifying said status data of patient to determine one or more occurrences of one or more physiological states of said status data of said patient; and
   II. classifying assessment content to determine one or more scores that are associated with one or more physiological states included in the one or more physiological states of said patient, wherein the assessment data includes information associated with one or more physiological states of the one or more physiological states of said patient; and
  C. providing one or more correlation values associated with the status data of patient based on historical status data content, assessment data, and scores;

D. employing the one or more correlation values to provide an amendment to said pharmaceutical dispensing regime, wherein the amendment includes one or more of an amendment in a pharmaceutical dispensing schedule, an amendment in a pharmaceutical dispensing quantity or an amendment in a pharmaceutical dispensing type of pharmaceutical; and E. instructing said pharmaceutical dispensing machine to dispense to said patient pharmaceuticals according to an amended pharmaceutical dispensing regime based on the correlation values, status data, assessment data and scores; and b. a patient assessment unit, comprising:
i. a plurality of sensors;
ii. a transceiver that communicates over a network;
iii. a memory that stores at least instructions;
iv. one or more processor devices that execute instructions that perform actions, including providing one or more physiological data or assessment data; and
v. at least one graphical user interface (GUI);

c. a dedicated personnel's device, comprising:
i. a transceiver that communicates over a network;
ii. a memory that stores at least instructions; and
iii. at least one graphical user interface (GUI);

d. a pharmaceutical dispensing machine comprising at least one pharmaceutical to be dispensed to said patient.

According to some embodiments of the invention, collecting status data of patient including physiological information associated with one or more physiological states of said patient includes:
a. receiving at least one physiological information related to said patient; and
b. generating the assessment data based on said at least one physiological information.

According to some embodiments of the invention, classifying the assessment data further comprises:
a. classifying physiological data provided by different sources; and
b. further determining the one or more scores based on the classification of the physiological data.

According to some embodiments of the invention, employing one or more assessment tool software to perform actions, further comprises:
a. providing real-time feedback to one or more subjects from which status data is being collected; and
b. collecting one or more responses from the one or more subjects that are associated with the real-time feedback.

According to some embodiments of the invention, further comprising updating the one or more classifiers based on the one or more correlation values.

According to some embodiments of the invention, employing one or more assessment tool software to perform actions, further comprises:
a. extracting a portion of the performance content associated with the assessment data based on the one or more scores that exceed a defined value; and
b. providing the extracted portion of the performance content and its assessment data to a classification processing engine for use as training data.

According to some embodiments of the invention, providing one or more correlation values associated with the status data, further comprises:
a. receiving a current physiological status that comprises one or more current physiological data;
b. correlating the current physiological status with at least one of historical status data content, assessment data, and scores; and
c. modifying the one or more classifiers based on the correlation of the current physiological status with said at least one of historical status data content, assessment data, and scores.

According to an aspect of some embodiments of the present invention there is provided a processor readable non-transitory storage media that includes instructions for assessing performances of physical activities, wherein execution of the instructions by one or more hardware processors performs actions comprising:
a. employing one or more assessment tool software to perform actions including:
i. collecting status data of patient including physiological information associated with one or more physiological states of said patient; said collecting is performed before commencing a pharmaceutical dispensing process;
ii. employing one or more classifiers to perform actions, including:
1. classifying said status data of patient to determine one or more occurrences of one or more physiological states of said status data of said patient; and
2. classifying assessment content to determine one or more scores that are associated with one or more physiological states included in the one or more physiological states of said patient, wherein the assessment data includes information associated with one or more physiological states of the one or more physiological states of said patient; and
iii. providing one or more correlation values associated with the status data of patient based on historical status data content, assessment data, and scores;
iv. employing the one or more correlation values to provide an amendment to said pharmaceutical dispensing regime, wherein the amendment includes one or more of an amendment in a pharmaceutical dispensing schedule, an amendment in a pharmaceutical dispensing quantity or an amendment in a pharmaceutical dispensing type of pharmaceutical; and
v. instructing said pharmaceutical dispensing machine to dispense to said patient pharmaceuticals according to an amended pharmaceutical dispensing regime based on the correlation values, status data, assessment data and scores.

According to some embodiments of the invention, collecting status data of patient including physiological information associated with one or more physiological states of said patient includes:
a. receiving at least one physiological information related to said patient; and
b. generating the assessment data based on said at least one physiological information.

According to some embodiments of the invention, classifying the assessment data further comprises:
a. classifying physiological data provided by different sources; and
b. further determining the one or more scores based on the classification of the physiological data.

According to some embodiments of the invention, employing one or more assessment tool software to perform actions, further comprises:
a. providing real-time feedback to one or more subjects from which status data is being collected; and b. collecting one or more responses from the one or more subjects that are associated with the real-time feedback.

According to some embodiments of the invention, further comprising updating the one or more classifiers based on the one or more correlation values.

According to some embodiments of the invention, employing one or more assessment tool software to perform actions, further comprises:

a. extracting a portion of the performance content associated with the assessment data based on the one or more scores that exceed a defined value; and b. providing the extracted portion of the performance content and its assessment data to a classification processing engine for use as training data.

According to some embodiments of the invention, providing one or more correlation values associated with the status data, further comprises:

a. receiving a current physiological status that comprises one or more current physiological data;

b. correlating the current physiological status with at least one of historical status data content, assessment data, and scores; and c. modifying the one or more classifiers based on the correlation of the current physiological status with said at least one of historical status data content, assessment data, and scores.

According to an aspect of some embodiments of the present invention there is provided a network computer for assessing performances of physical activities, comprising:

a. a transceiver that communicates over the network;

b. a memory that stores at least instructions; and c. one or more processor devices that execute instructions that perform actions, including:

i. employing one or more assessment tool software to perform actions including:
    1. collecting status data of patient including physiological information associated with one or more physiological states of said patient; said collecting is performed before commencing a pharmaceutical dispensing process;
  ii. employing one or more classifiers to perform actions, including:
    2. classifying said status data of patient to determine one or more occurrences of one or more physiological states of said status data of said patient; and
    3. classifying assessment content to determine one or more scores that are associated with one or more physiological states included in the one or more physiological states of said patient, wherein the assessment data includes information associated with one or more physiological states of the one or more physiological states of said patient; and
  iii. providing one or more correlation values associated with the status data of patient based on historical status data content, assessment data, and scores;
  iv. employing the one or more correlation values to provide an amendment to said pharmaceutical dispensing regime, wherein the amendment includes one or more of an amendment in a pharmaceutical dispensing schedule, an amendment in a pharmaceutical dispensing quantity or an amendment in a pharmaceutical dispensing type of pharmaceutical; and
  v. instructing said pharmaceutical dispensing machine to dispense to said patient pharmaceuticals according to an amended pharmaceutical dispensing regime based on the correlation values, status data, assessment data and scores.

According to some embodiments of the invention, collecting status data of patient including physiological information associated with one or more physiological states of said patient includes:

a. receiving at least one physiological information related to said patient; and b. generating the assessment data based on said at least one physiological information.

According to some embodiments of the invention, classifying the assessment data further comprises:

a. classifying physiological data provided by different sources; and b. further determining the one or more scores based on the classification of the physiological data.

According to some embodiments of the invention, employing one or more assessment tool software to perform actions, further comprises:

a. providing real-time feedback to one or more subjects from which status data is being collected; and b. collecting one or more responses from the one or more subjects that are associated with the real-time feedback.

According to some embodiments of the invention, further comprising updating the one or more classifiers based on the one or more correlation values.

According to some embodiments of the invention, employing one or more assessment tool software to perform actions, further comprises:

a. extracting a portion of the performance content associated with the assessment data based on the one or more scores that exceed a defined value; and b. providing the extracted portion of the performance content and its assessment data to a classification processing engine for use as training data.

According to some embodiments of the invention, providing one or more correlation values associated with the status data, further comprises:

a. receiving a current physiological status that comprises one or more current physiological data;

b. correlating the current physiological status with at least one of historical status data content, assessment data, and scores; and c. modifying the one or more classifiers based on the correlation of the current physiological status with said at least one of historical status data content, assessment data, and scores.

According to an aspect of some embodiments of the present invention there is provided a system for assessing a pharmaceutical dispensing regime to be dispensed by a pharmaceutical dispensing machine, comprising:

a. an automatic pharmaceutical dispensing assessment unit for a pharmaceutical dispensing system that performs at least one pharmaceutical dispensing process, the unit comprising:
  i. at least one processor device;
  ii. at least one computer readable medium having computer program instructions thereon;
  iii. at least one communication unit in communication with:
    A. at least one server of a pharmaceutical dispensing system; and
    B. at least one patient assessment unit;
    C. at least one pharmaceutical dispensing machine;
  wherein said at least one processor device execute said program instructions to perform actions, including:
    iv. receiving at least one pharmaceutical dispensing regime for at least one patient from at least one physician; said at least one pharmaceutical dispensing regime comprising at least one pharmaceutical dispensing schedule comprising at least one time of dispensing pharmaceuticals, at least one pharmaceutical and at least one pharmaceutical dispensing quantity;
v. automatically assessing a status of said patient by collecting status information of said patient by said at least one patient assessment unit at a determined time before said time of dispensing pharmaceuticals and before said pharmaceutical dispensing machine commences said pharmaceutical dispensing process;
vi. automatically assessing when said status of said patient affects said at least one pharmaceutical dispensing regime;
vii. automatically amending said at least one pharmaceutical dispensing regime according to said status of said patient to create at least one amended pharmaceutical dispensing regime when said status of said patient affects said at least one pharmaceutical dispensing regime;
viii. dispensing by said pharmaceutical dispensing machine said at least one pharmaceutical according to said at least one amended pharmaceutical dispensing regime;
b. a patient assessment unit, comprising:
i. a plurality of sensors;
ii. a transceiver that communicates over a network;
iii. a memory that stores at least instructions;
iv. one or more processor devices that execute instructions that perform actions, including providing one or more physiological data or assessment data; and
v. at least one graphical user interface (GUI);
c. a dedicated personnel's device, comprising:
i. a transceiver that communicates over a network;
ii. a memory that stores at least instructions; and
iii. at least one graphical user interface (GUI);
d. a pharmaceutical dispensing machine comprising at least one pharmaceutical to be dispensed to said patient.

According to some embodiments of the invention, said automatic pharmaceutical dispensing assessment unit is located within said pharmaceutical dispensing machine.

According to some embodiments of the invention, said automatic pharmaceutical dispensing assessment unit is located outside said pharmaceutical dispensing machine.

According to some embodiments of the invention, said automatic pharmaceutical dispensing assessment unit is located at a remote location and in direct communication with said pharmaceutical dispensing machine.

According to some embodiments of the invention, said automatically assessing a status of said patient comprises performing at least one test and said determined time before said time of dispensing is relative to the time required to receive results of said test.

According to some embodiments of the invention, said determined time before said time of dispensing is relative to the time required for the pharmaceutical dispensing machine to finish said pharmaceutical dispensing process.

According to some embodiments of the invention, automatically assessing a status of said patient comprises measuring at least one physiological parameter of said patient.

According to some embodiments of the invention, automatically assessing a status of said patient comprises measuring at least one behavioral parameter of said patient.

According to some embodiments of the invention, said automatically assessing a status of said patient comprises connecting said patient to at least one sensor.

According to some embodiments of the invention, said at least one sensor is selected from the group consisting of thermometer, weight meter, blood pressure sensor, sleep sensor, movement sensor, cardiac activity sensor, neuro-activity sensor, muscle activity sensor, breathing sensor, invasive blood test sensor, external blood test sensor, acoustical sensor, imaging sensor for detection of ear infections, imaging sensor for detection of throat infections, epileptic seizure sensor, drug level in blood assessment sensor, a swallowed sensor comprising a plurality of sensors in it and any combination thereof.

According to some embodiments of the invention, said status information comprises at least one selected from the group consisting of temperature, weight, blood pressure, sleeping patterns, movement patterns, cardiac activity, neurological activity, muscle activity, breathing patterns, blood content, acoustical data, ear infection status, throat infection status, epileptic activity, drug levels in the blood and any combination thereof.

According to some embodiments of the invention, automatically amending said at least one pharmaceutical dispensing regime further comprises notifying said at least one physician of said at least one amended pharmaceutical dispensing regime.

According to some embodiments of the invention, said determined time before said time of dispensing is from about 1 minute to about 3 hours.

According to some embodiments of the invention, said automatically assessing a status of said patient comprises sending information about said assessment status to at least one server to be analyzed by an assessment tool software.

According to some embodiments of the invention, said automatically assessing a status of said patient further comprises revising if said physician provided conditions on which said pharmaceutical dispensing regime needs to be amended according to a status of the patient close to the time of dispensing pharmaceuticals.

According to some embodiments of the invention, said automatically assessing when said status of said patient affects said at least one pharmaceutical dispensing regime comprises comparing said status information with data located in said server.

According to some embodiments of the invention, said automatically assessing when said status of said patient affects said at least one pharmaceutical dispensing regime comprises comparing said status information with historical status data content.

According to some embodiments of the invention, said automatically assessing when said status of said patient affects said at least one pharmaceutical dispensing regime comprises comparing said status information with assessment data.

According to some embodiments of the invention, said automatically assessing when said status of said patient affects said at least one pharmaceutical dispensing regime comprises comparing said status information with status information from other patients in the vicinity of said patient.

According to some embodiments of the invention, said method further comprises updating said database with data received during the managing of said pharmaceutical dispensing process.

According to an aspect of some embodiments of the present invention there is provided a method of managing a pharmaceutical dispensing process performed by a pharmaceutical dispensing machine, comprising:

a. receiving at least one pharmaceutical dispensing regime for at least one patient from at least one physician; said at least one pharmaceutical dispensing regime comprising at least one pharmaceutical dispensing schedule comprising at least one time of dispensing pharmaceuticals, at least one pharmaceutical and at least one pharmaceutical dispensing quantity;

b. assessing a status of said patient by collecting status information of said patient at a determined time before said time of dispensing pharmaceuticals and before said pharmaceutical dispensing machine commences said pharmaceutical dispensing process;

c. automatically assessing when said status of said patient affects said at least one pharmaceutical dispensing regime;

d. amending said at least one pharmaceutical dispensing regime according to said status of said patient to create at least one amended pharmaceutical dispensing regime when said status of said patient affects said at least one pharmaceutical dispensing regime;

e. dispensing by said pharmaceutical dispensing machine said at least one pharmaceutical according to said at least one amended pharmaceutical dispensing regime.

According to some embodiments of the invention, said assessing a status of said patient is automatically performed.

According to some embodiments of the invention, said amending said at least one pharmaceutical dispensing regime is automatically performed.

According to some embodiments of the invention, said assessing a status of said patient comprises performing at least one test and said determined time before said time of dispensing is relative to the time required to receive results of said test.

According to some embodiments of the invention, said determined time before said time of dispensing is relative to the time required for the pharmaceutical dispensing machine to finish said pharmaceutical dispensing process.

According to some embodiments of the invention, said assessing a status of said patient comprises measuring at least one physiological parameter of said patient.

According to some embodiments of the invention, said assessing a status of said patient comprises connecting said patient to at least one sensor.

According to some embodiments of the invention, amending said at least one pharmaceutical dispensing regime further comprises notifying said at least one physician of said at least one amended pharmaceutical dispensing regime.

According to some embodiments of the invention, said assessing a status of said patient comprises sending information about said assessment status to at least one server to be analyzed by an assessment tool software.

According to some embodiments of the invention, said assessing a status of said patient further comprises revising if said physician provided conditions on which said pharmaceutical dispensing regime needs to be amended according to a status of the patient close to the time of dispensing pharmaceuticals.

According to some embodiments of the invention, said assessing when said status of said patient affects said at least one pharmaceutical dispensing regime comprises comparing said status information with data located in a server.

According to some embodiments of the invention, said assessing when said status of said patient affects said at least one pharmaceutical dispensing regime comprises comparing said status information with historical status data content.

According to some embodiments of the invention, said assessing when said status of said patient affects said at least one pharmaceutical dispensing regime comprises comparing said status information with assessment data.

According to some embodiments of the invention, said assessing when said status of said patient affects said at least one pharmaceutical dispensing regime comprises comparing said status information with status information from other patients in the vicinity of said patient.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

As will be appreciated by one skilled in the art, some embodiments of the present invention may be embodied as a system, method or computer program product. Accordingly, some embodiments of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, some embodiments of the present invention may take the form of a computer program product embodied in one or more computer readable medium(s) having computer readable program code embodied thereon. Implementation of the method and/or system of some embodiments of the invention can involve performing and/or completing selected tasks manually, automatically, or a combination thereof. Moreover, according to actual instrumentation and equipment of some embodiments of the method and/or system of the invention, several selected tasks could be implemented by hardware, by software or by firmware and/or by a combination thereof, e.g., using an operating system.

For example, hardware for performing selected tasks according to some embodiments of the invention could be implemented as a chip or a circuit. As software, selected tasks according to some embodiments of the invention could be implemented as a plurality of software instructions being executed by a computer using any suitable operating system. In an exemplary embodiment of the invention, one or more tasks according to some exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

Any combination of one or more computer readable medium(s) may be utilized for some embodiments of the invention. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium and/or data used thereby may be transmitted using any appropriate medium, including but not limited to wireless, wireline, optical fiber cable, RF, etc., or any suitable combination of the foregoing.

Computer program code for carrying out operations for some embodiments of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Some embodiments of the present invention may be described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Some of the methods described herein are generally designed only for use by a computer, and may not be feasible or practical for performing purely manually, by a human expert. A human expert who wanted to manually perform similar tasks, might be expected to use completely different methods, e.g., making use of expert knowledge and/or the pattern recognition capabilities of the human brain, which would be vastly more efficient than manually going through the steps of the methods described herein.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 12:
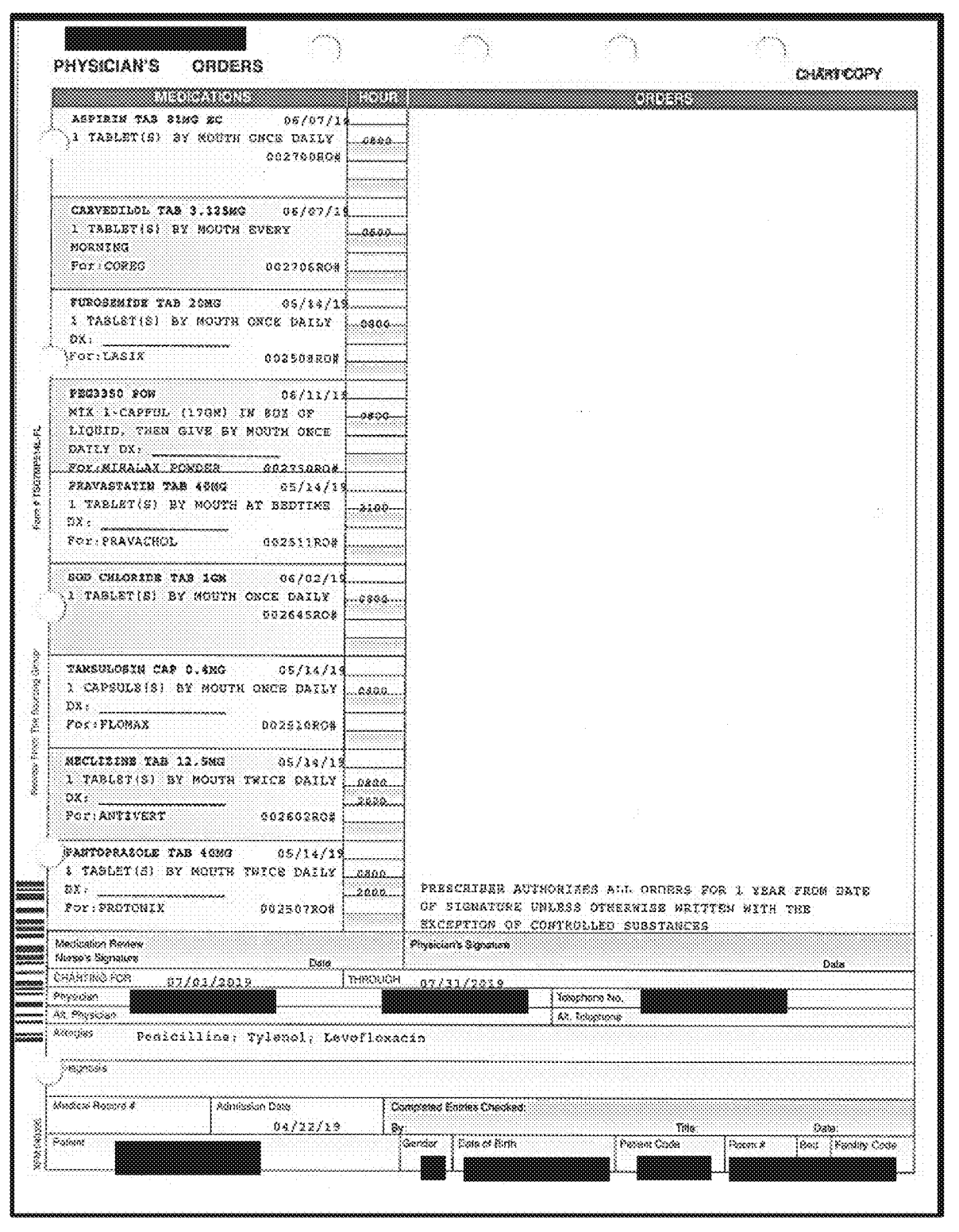

FIG. 12 is an exemplary drug prescription order provided by a physician.

DESCRIPTION OF SPECIFIC EMBODIMENTS OF THE INVENTION

Figure 1:
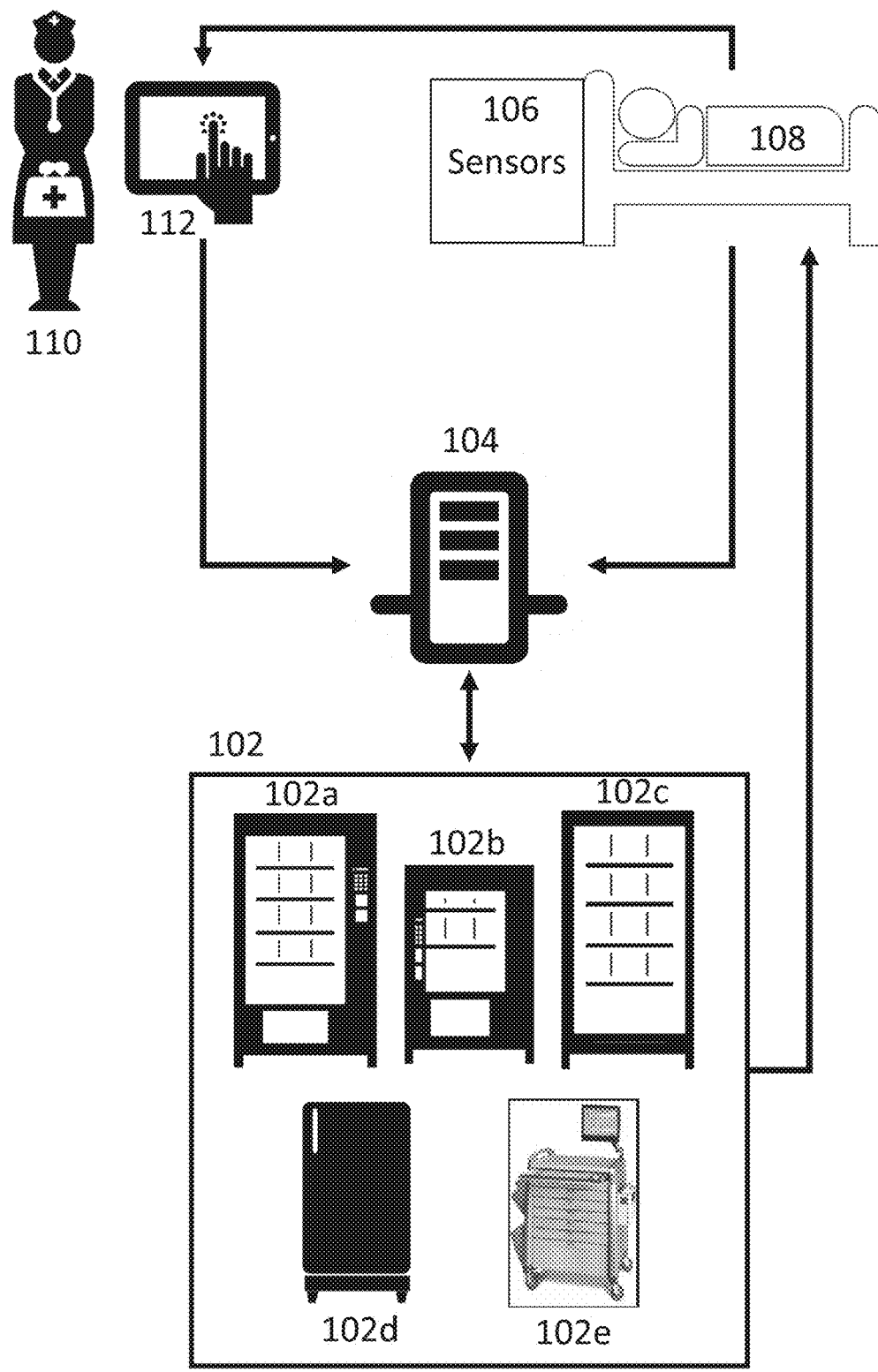
FIG. 1 is a system block diagram of a pharmaceutical dispensing system 100, according to some embodiments of the claimed invention.

The present invention, in some embodiments thereof, relates to a pharmaceutical dispensing system and, more particularly, but not exclusively, to a pharmaceutical dispensing system with dynamic pharmaceutical dispensing regimes.

Overview

An aspect of some embodiments of the invention relates to automatically amending a pharmaceutical dispensing regime of a patient, the pharmaceutical dispensing regime provided by a physician, the amendment to the pharmaceutical dispensing regime is performed before the beginning of the pharmaceutical dispensing process by a pharmaceutical dispensing machine and according to an assessment of the status of the patient. In some embodiments, dispensing of the pharmaceuticals is performed according to the amended pharmaceutical dispensing regime. In some embodiments, the physician is notified and/or is required to confirm an amendment to the pharmaceutical dispensing regime. In some embodiments, a plurality of possible amendments of the pharmaceutical dispensing regime are provided a priori by the physician. In some embodiments, the plurality of possible amendments of the pharmaceutical dispensing regime are based on estimations of possible scenarios provided by the physician. In some embodiments, the plurality of amendments of the pharmaceutical dispensing regime are based on previous similar cases. In some embodiments, the amendment of the pharmaceutical dispensing regime is due to changes in the physiological status of the patient before the pharmaceutical dispensing time. In some embodiments, assessment of the physiological status of the patient, before dispensing the pharmaceuticals, is performed by measuring at least one of vital signs, temperature, behavior and/or blood content. In some embodiments, amendments in the pharmaceutical dispensing regime are performed by comparing the current physiological status of the patient with at least one reference data, and amending said pharmaceutical dispensing regime according to predetermined alternative pharmaceutical dispensing regimes when said current physiological status differs from said reference data, and dispensing pharmaceuticals according to the amended pharmaceutical dispensing regime.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Generic Overview of System

Referring now to the drawings, FIG. 1 illustrates a generic flowchart of a pharmaceutical dispensing system 100, according to some embodiments of the claimed invention. In some embodiments, the pharmaceutical dispensing system comprises at least one pharmaceutical dispensing machine 102. In some embodiments, the at least one pharmaceutical dispensing machine is located at the same location as the patient, optionally in close proximity to the patient. In some embodiments, the pharmaceutical dispensing machine is located at a different location as the patient, and optionally drug transportation is needed to provide the dispensed pharmaceuticals to the patient. Optionally, the system comprises a plurality of pharmaceutical dispensing machines, for example a large pharmaceutical dispensing machine 102*a*, which is adapted to store, package and dispense a large quantity of pharmaceuticals; a small pharmaceutical dispensing machine 102*b*, which comprises the same capabilities of the large machine 102*a* but with fewer pharmaceuticals in it; a bulk storage cabinet 102*c*, which comprises a variety of pharmaceuticals and medical materials (e.g. liquid drugs, IV, bandages, insulin, pill storage) in bulk; a refrigerator 102*d*, which comprises a variety of pharmaceuticals and/or medical materials that require special storage temperatures; a nursing cart 102*e*, which are optionally locked and opened by adapted and authorized personnel. In some embodiments, authorized personnel can be a nurse, a physician or any other authorized personnel.

As used herein, the term "dedicated personnel" and/or "physician" and/or "doctor" and/or "nurse" may refer to an individual that has acquired, either through specialized education, experience, and/or training, a level of expertise in regards to the subject activity. A dedicated personnel may be qualified to provide assessment data documenting the subject physiological status and provide an assessment to aspects or domains of the subject physiological status that require expert-level judgement. A dedicated personnel may be a doctor, a nurse and/or a pharmacist. A dedicated personnel may be known to the subject or may be completely anonymous.

In some embodiments, any of the above dispensing machines and/or storage units assists in the pharmaceutical dispensing service. In some embodiments, different devices of the system are used in combination to provide the pharmaceuticals in the pharmaceutical dispensing service. In some embodiments, each of the abovementioned devices is monitored and controlled by the system. In some embodiments, any of the above dispensing machines and/or storage units comprise a plurality of pharmaceuticals according to their physical capacities, for example, certain dispensing machine may comprise 30 different pharmaceuticals, while other may comprise 100 or 300 or any quantity of different pharmaceuticals. In some embodiments, the small and/or the large pharmaceutical dispensing machine packages pharmaceuticals as the circumstance arises (also known as PRN— "pro re nata") and/or first dose pharmaceuticals for a single patient. In some embodiments, adapted and authorized personnel can access the bulk storage cabinet 102*c* when necessary. In some embodiments, adapted and authorized personnel can access the refrigerator 102*d* when necessary.

In some embodiments, the at least one pharmaceutical dispensing machine 102 is connected to at least one server 104. In some embodiments, the server comprises all the information regarding users, patients, personnel, pharmaceuticals, insurance, budget, costs, timetables for pharmaceutical deliveries from suppliers; also past, present and future information regarding pharmaceutical needs with relation to patients and the cases related to those needs.

In some embodiments, the server 104 includes an assessment tool software.

In some embodiments, the assessment tool software includes patient classifiers, pharmaceutical classifiers, physiological classifiers and a classification processing engine. In some embodiments, patient classifiers process patient's data. For example, patient classifiers identify positive, negative, or neutral aspects related to the patient, as well as severity and/or relativity (e.g. age, sex, physical condition, previous interventions, family history, etc.). In some embodiments, pharmaceutical classifiers identify positive, negative, or neutral aspects related to pharmaceuticals. For example, active ingredients, optimal dosage, contraindications, scope of the pharmaceutical, etc. In some embodiments, physiological classifiers identify positive, negative, or neutral aspects related to physiological data. For example, diseases, symptoms, treatments related to symptoms, sleep patterns, psychological states, etc. In some embodiment, classifiers refer to machine learning systems, e.g. neural networks that have been trained with a "ground truth" to identify certain features. In the context of pharmaceutical dispensing regimes, for example, a machine learning system may be trained with previous cases data, actions taken and outcomes, along with an indication (i.e. ground truth) that a human expert has identified the information as valid for use in pharmaceutical dispensing regimes. By applying machine learning techniques, these classifiers process this input, and can then be used to identify, to a level of confidence, the best course of action in a specific situation.

In some embodiments, classifiers are used to determine one or more scores associated with one or more physiological states included in the one or more physiological states of said patient. In some embodiments, the scores are also associated with one or more pharmaceuticals. In some embodiments, the scores are also associated with one or more diseases, symptoms, treatments related to symptoms, sleep patterns, psychological states, etc. In some embodiments, the scores are also associated with one or more pharmaceutical dispensing regimes related to one or more pathologies.

In some embodiments, the classification processing engine analyzes the classification results, including by aggregating identified features and comparing, among and between subjects, classifications of the same or different pharmaceutical dispensing regimes. In some embodiments, classification processing engine also collate dedicated personnel data and/or generate, provide, and/or receive reports based on the dedicated personnel data. In some embodiments, providing one or more correlation values associated with the status data of patient are based on comparison with historical status data content, assessment data, and scores.

In some embodiments, the patient assessment unit controls or performs various portions of automated assessment of operator performance.

In some embodiments, the pharmaceutical assessment unit is located within said pharmaceutical dispensing machine. In some embodiments, the pharmaceutical assessment unit is located outside said pharmaceutical dispensing machine. In some embodiments, the pharmaceutical assessment unit is located at a remote location and in direct communication with said pharmaceutical dispensing machine.

In some embodiments, a plurality of sensors and measuring devices 106 are connected or are in physical communication with the patient 108 and are adapted to measure and collect a plurality of data regarding the physiological, physical and mental state of the patient 108 at any moment. In some embodiments, the plurality of sensors are unified in the patient assessment unit. In some embodiments, the measurements collected by the patient assessment unit are sent to the server 104 in order to be analyzed by the assessment tool software.

In some embodiments, dedicated personnel 110 that monitor the patient, can access the pharmaceutical dispensing system using dedicated hardware/software 112 using a dedicated graphical user interface (GUI). In some embodiments, the GUI can be a tablet, a smartphone and/or a computer. In some embodiments, the GUI is a device located near the bed of the patient. In some embodiments, the pharmaceutical dispensing system can be accessed remotely using any kind of electronic device using cloud-based technology.

Exemplary General Overview of Pharmaceutical Dispensing Methods

Figure 2:
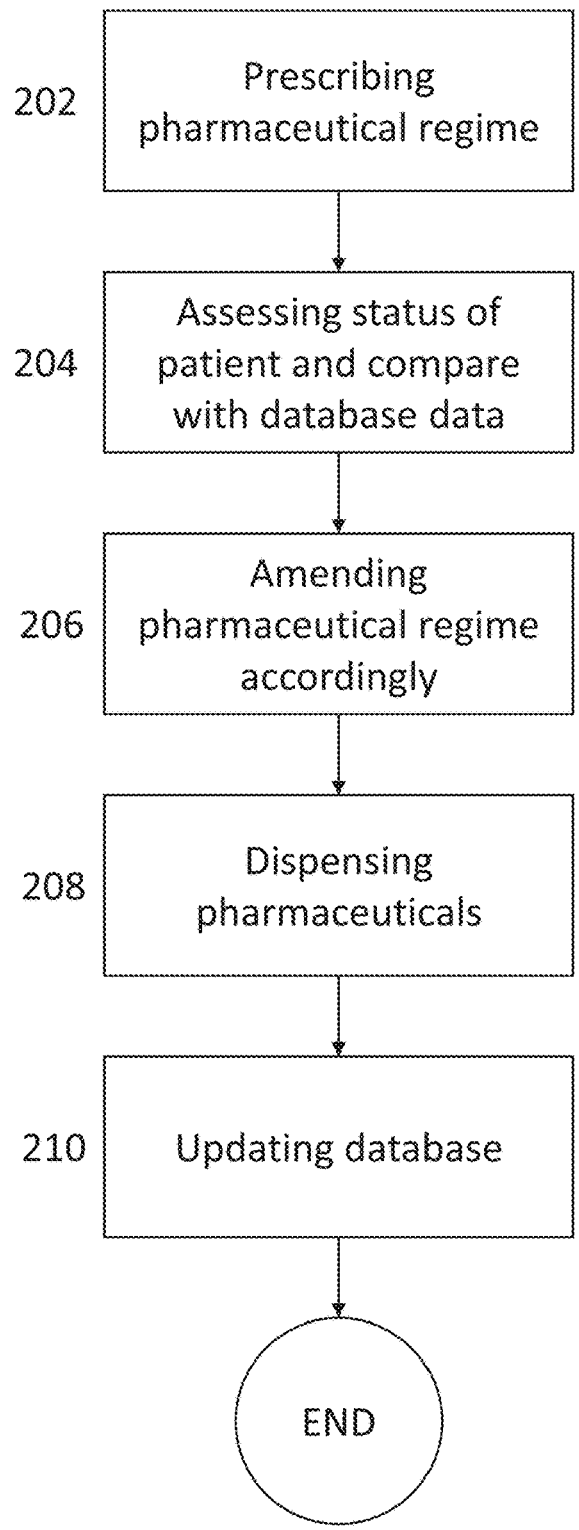
FIG. 2 is a schematic flowchart of a pharmaceutical dispensing method, according to some embodiments of the present invention.
Figure 3:
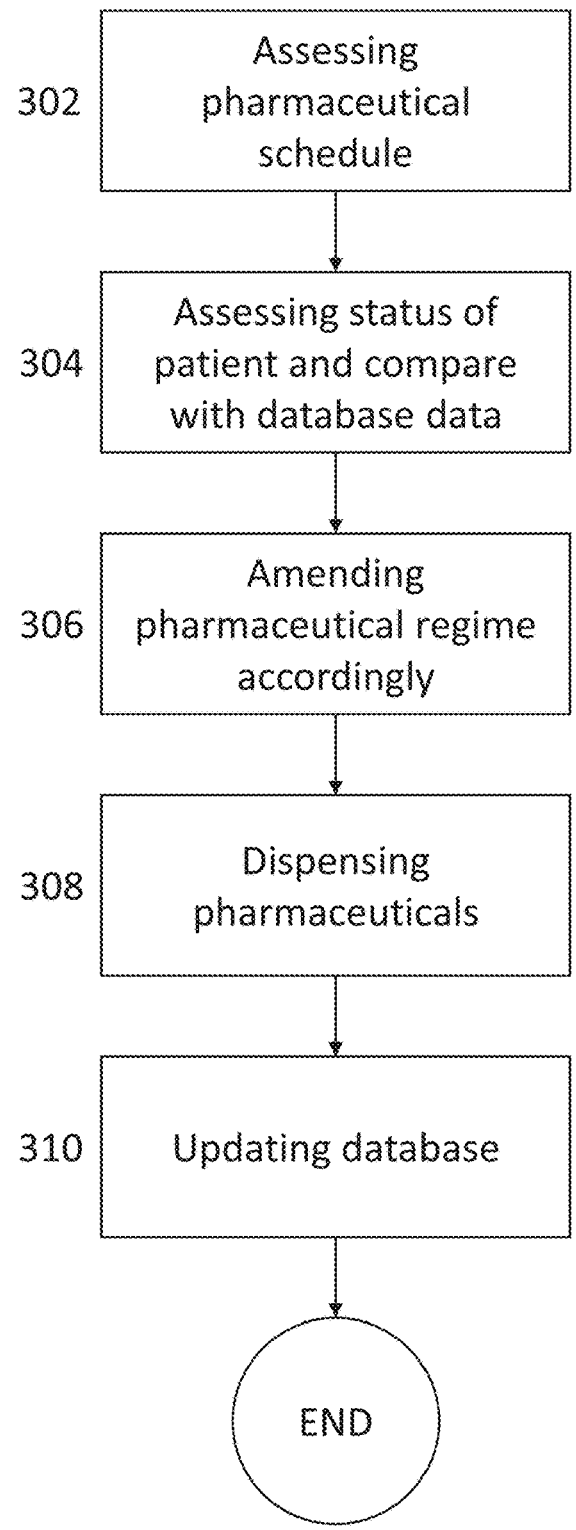
FIG. 3 is a schematic flowchart of a pharmaceutical dispensing method, according to some embodiments of the present invention.
Figure 4:
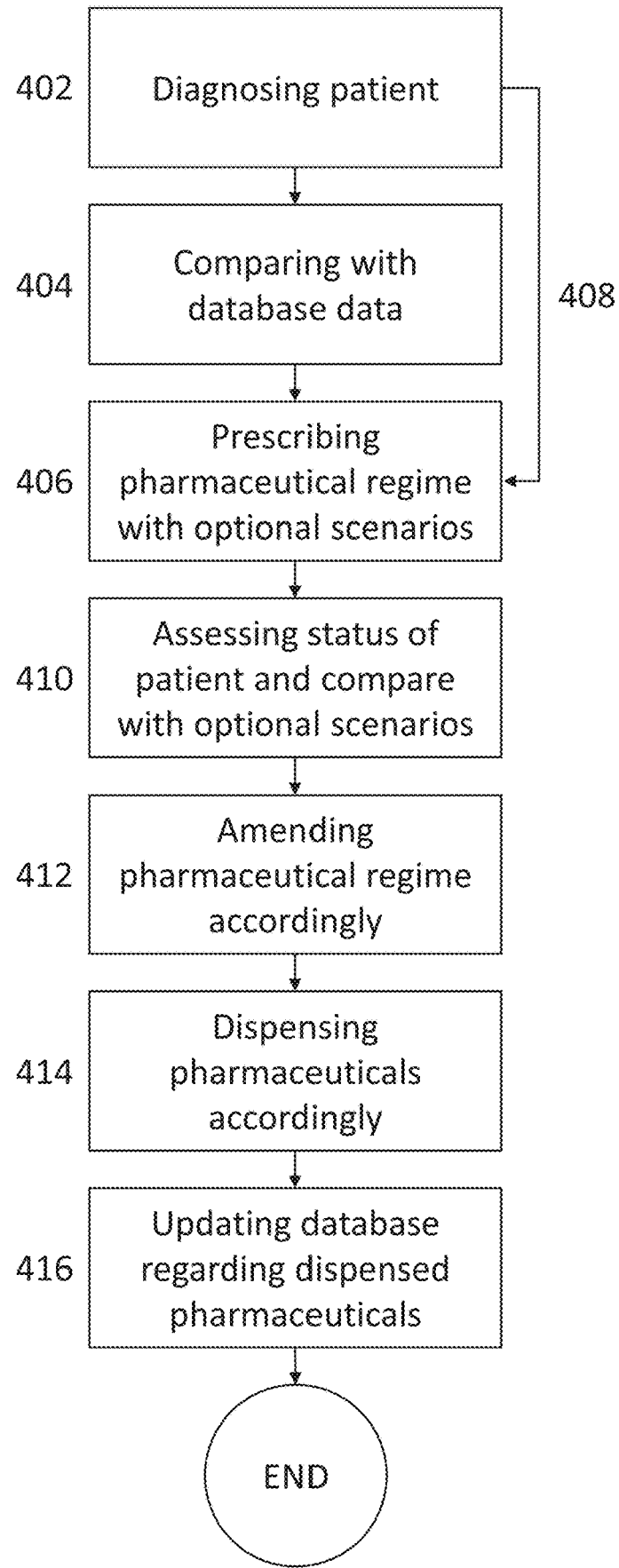
FIG. 4 is a schematic flowchart of a pharmaceutical dispensing method, according to some embodiments of the present invention.

FIGS. 2-4 illustrate general overviews of pharmaceutical dispensing methods that, in some embodiments, are performed separately, and optionally, the methods can be performed in parallel/or in combination.

Referring to FIG. 2, in some embodiments, the pharmaceutical dispensing method 200 comprises prescribing a pharmaceutical dispensing regime to a patient 202. For example, the physician periodically provides orders of pharmaceuticals that need to be dispensed to the patient. In some embodiments, the orders are based on the physician's evaluation of the patient condition. An actual example of such order can be seen in FIG. 12 (sensitive information has been cancelled due to privacy). In some embodiments, the pharmaceutical dispensing regime comprises dispensing at least one pharmaceutical. In some embodiments, when prescribing the pharmaceutical dispensing regime, the doctor and/or the personnel provide the type of pharmaceutical, the frequency of consumption, the time of consumption of the pharmaceutical and optionally the conditions on which the dispensing regime needs to change according to the status of the patient close to the time of dispensing.

In some embodiments, close to the time of dispensing of the pharmaceutical, the system assesses the status of the patient and compares the data received with data located in the database 204. In some embodiments, close to the time of dispensing is from about 1 minute to about 3 hours before the dispensing time. Optionally, close to the time of dispensing is from about 30 minutes to about 5 hours before the dispensing time. Optionally, close to the time of dispensing is from about 10 minutes to about 8 hours before the dispensing time. For example, close to the time of dispensing can be 1 minute before, 10 minutes before, 30 minutes before, 1 hour before, 3 hours before. In some embodiments, close to the time of dispensing is decided according to the time required for the pharmaceutical dispensing machine to prepare all the scheduled pharmaceuticals for the time of dispensing. In some embodiments, assessing the status of the patient comprises assessing the physiological and/or physical and/or psychological status of the patient. In some embodiments, assessing the status of the patient comprises attaching dedicated devices configured to measure the status (either physiological and/or physical) of the patient.

Optionally, the dedicated devices are activated and monitored by the system without intervention from the doctor and/or the personnel. In some embodiments, assessing the status of the patient comprises taking blood, urine samples and/or fecal samples from the patient and sending it to the laboratory for analysis. In some embodiments, the system takes includes the time required for the laboratory to provide results to begin the assessment of the patient before the scheduled dispensing of the pharmaceuticals. In some embodiments, the data from the database comprises, for example, previous data from the same patient, data from other patients having similar diagnosis, data from scientific and medical publications, data manually inserted by the doctor and/or personnel. In some embodiments, the doctor and/or personnel provides comparison parameters used to evaluate the received data from the patient's assessment in comparison with the data located in the database. In some embodiments, comparison parameters are a range of values, for example, the temperature of the patient is from about 37.9 Celsius to about 38.5 Celsius. In some embodiments, comparison parameters are a plurality of ranges of values, for example, the temperature of the patient is from about 37.9 Celsius to about 38.5 Celsius, or from about 38.6 Celsius to about 39.5 Celsius. In some embodiments, comparison parameters are a certain parameter that must be achieved, for example, the temperature of the patient is higher than 38 Celsius. In some embodiments, comparison parameters can be a combination of ranges and specific parameters, for example, the temperature of the patient is from about 37.9 Celsius to about 38.5 Celsius, or from about 38.6 Celsius to about 39.5 Celsius, or higher than 39.5.

In some embodiments, when the comparison of the data received from the assessment of the patient and the data located in the database falls either between the predetermined range/ranges or falls below or above a predetermined value, the system amends the pharmaceutical dispensing regime accordingly 206. In some embodiments, the database comprises the required information to correctly amend the pharmaceutical dispensing regime. In some embodiments, the information required to correctly amend the pharmaceutical dispensing regime is provided by the doctor and/or the personnel. Optionally, the information is provided by the doctor and/or personnel a priori. In some embodiments, the information required to correctly amend the pharmaceutical dispensing regime is recovered from past cases. In some embodiments, the information required to correctly amend the pharmaceutical dispensing regime is a combination of the above, for example, the system recovers information on how to amend the pharmaceutical dispensing regime and then transmit the information to the doctor and/or personnel for approval (see below for more information on this).

In some embodiments, after the pharmaceutical dispensing regime has been amended accordingly, the system continues to dispense the pharmaceuticals according to the regime 208. Lastly, the system updates the database 210 with the information regarding the patient, the data from the assessment and the amendment on the pharmaceutical regime, to be used later on, for the monitoring of the patient and/or for use as reference for future cases.

Referring to FIG. 3, in some embodiments, the pharmaceutical dispensing method 300 comprises assessing the pharmaceutical dispensing schedule for at least one patient 302. In some embodiments, this method is used after the prescription for the at least one patient was provided by the doctor and/or the personnel, for example, a patient recovering from a chirurgical intervention is required to receive anticoagulants three times a day for seven days while still in the hospital and it is day three of the recovery, the system assesses the pharmaceutical schedule for dispensing pharmaceuticals, and in this example, is the dispensing of anticoagulants in the morning for the patient that had the intervention.

In some embodiments, similar to the method disclosed above, close to the time of dispensing of the pharmaceutical, the system assesses the status of the patient and compares the data received with data located in the database 304. In some embodiments, the assessment is based on the patient's information as received from at least one or all the measurements and/or sensors. In some embodiments, additionally or optionally, the assessment takes under consideration the condition of other patients in the same site. For example, making an assessment by taking into consideration if there is an infective disease affecting more than one patient in the same facility, and providing a treatment accordingly. In some embodiments, the assessment also takes under consideration previous assessments made by the same physician and/or other physicians for the same pathology. In some embodiments, close to the time of dispensing is from about 1 minute to about 3 hours before the dispensing time. Optionally, close to the time of dispensing is from about 30 minutes to about 5 hours before the dispensing time. Optionally, close to the time of dispensing is from about 10 minutes to about 8 hours before the dispensing time. For example, close to the time of dispensing can be 1 minute before, 10 minutes before, 30 minutes before, 1 hour before, 3 hours before.

In some embodiments, close to the time of dispensing is decided according to the time required for the pharmaceutical dispensing machine to prepare all the scheduled pharmaceuticals for the time of dispensing. In some embodiments, assessing the status of the patient comprises assessing the physiological and/or physical and/or psychological status of the patient. In some embodiments, assessing the status of the patient comprises attaching dedicated devices configured to measure the status (either physiological and/or physical) of the patient. Optionally, the dedicated devices are activated and monitored by the system without intervention from the doctor and/or the personnel. In some embodiments, assessing the status of the patient comprises taking blood from the patient and sending it to the laboratory for analysis. In some embodiments, the system takes includes the time required for the laboratory to provide results to begin the assessment of the patient before the scheduled dispensing of the pharmaceuticals.

In some embodiments, the data from the database comprises, for example, previous data from the same patient, data from other patients having similar diagnosis, data from scientific and medical publications, data manually inserted by the doctor and/or personnel.

In some embodiments, the doctor and/or personnel provides comparison parameters used to evaluate the received data from the patient's assessment in comparison with the data located in the database. In some embodiments, comparison parameters are a range of values, for example, the temperature of the patient is from about 37.9 Celsius to about 38.5 Celsius. In some embodiments, comparison parameters are a plurality of ranges of values, for example, the temperature of the patient is from about 37.9 Celsius to about 38.5 Celsius, or from about 38.6 Celsius to about 39.5 Celsius. In some embodiments, comparison parameters are a certain parameter that must be achieved, for example, the temperature of the patient is higher than 38 Celsius. In some embodiments, comparison parameters can be a combination of ranges and specific parameters, for example, the temperature of the patient is from about 37.9 Celsius to about 38.5 Celsius, or from about 38.6 Celsius to about 39.5 Celsius, or higher than 39.5.

In some embodiments, when the comparison of the data received from the assessment of the patient and the data located in the database falls either between the predetermined range/ranges or falls below or above a predetermined value, the system amends the pharmaceutical dispensing regime accordingly 306. In some embodiments, the database comprises the required information to correctly amend the pharmaceutical dispensing regime. In some embodiments, the information required to correctly amend the pharmaceutical dispensing regime is provided by the doctor and/or the personnel. Optionally, the information is provided by the doctor and/or personnel a priori. In some embodiments, the information required to correctly amend the pharmaceutical dispensing regime is recovered from past cases. In some embodiments, the information required to correctly amend the pharmaceutical dispensing regime is a combination of the above, for example, the system recovers information on how to amend the pharmaceutical dispensing regime and then transmit the information to the doctor and/or personnel for approval (see below for more information on this).

In some embodiments, after the pharmaceutical dispensing regime has been amended accordingly, the system continues to dispense the pharmaceuticals according to the regime 308. Lastly, the system updates the database 310 with the information regarding the patient, the data from the assessment and the amendment on the pharmaceutical regime, to be used later on, for the monitoring of the patient and/or for use as reference for future cases.

Referring to FIG. 4, in some embodiments, the pharmaceutical dispensing method 400 begins with the doctor diagnosing a patient 402, for example, the doctor diagnoses a patient with high blood pressure and he is interested in prescribing a pharmacological agent to treat the blood pressure. The patient also suffers from acute myalgia and he is being pharmacologically treated for it. In some embodiments, at this point the doctor can access the database and compare this data with data already found in the database 404, and try to find possible solutions and/or past cases, when a patient that pharmacologically treated for myalgia needs to take blood pressure pharmaceuticals. In some embodiments, the system provides possible solutions and the doctor can then prescribe a pharmaceutical regime accordingly 406. In some embodiments, the doctor can prescribe a pharmaceutical regime without consulting the system with regards of past cases 408.

In some embodiments, similar to the method disclosed above, close to the time of dispensing of the pharmaceutical, the system assesses the status of the patient and compares the data received with data located in the database 410. In some embodiments, close to the time of dispensing is from about 1 minute to about 3 hours before the dispensing time. Optionally, close to the time of dispensing is from about 30 minutes to about 5 hours before the dispensing time. Optionally, close to the time of dispensing is from about 10 minutes to about 8 hours before the dispensing time. For example, close to the time of dispensing can be 1 minute before, 10 minutes before, 30 minutes before, 1 hour before, 3 hours before. In some embodiments, close to the time of dispensing is decided according to the time required for the pharmaceutical dispensing machine to prepare all the scheduled pharmaceuticals for the time of dispensing. In some embodiments, assessing the status of the patient comprises assessing the physiological and/or physical and/or psychological status of the patient. In some embodiments, assessing the status of the patient comprises attaching dedicated devices configured to measure the status (either physiological and/or physical) of the patient.

Optionally, the dedicated devices are activated and monitored by the system without intervention from the doctor and/or the personnel. In some embodiments, assessing the status of the patient comprises taking blood from the patient and sending it to the laboratory for analysis. In some embodiments, the system takes includes the time required for the laboratory to provide results to begin the assessment of the patient before the scheduled dispensing of the pharmaceuticals. In some embodiments, the data from the database comprises, for example, previous data from the same patient, data from other patients having similar diagnosis, data from scientific and medical publications, data manually inserted by the doctor and/or personnel. In some embodiments, the doctor and/or personnel provides comparison parameters used to evaluate the received data from the patient's assessment in comparison with the data located in the database.

In some embodiments, comparison parameters are a range of values, for example, the temperature of the patient is from about 37.9 Celsius to about 38.5 Celsius. In some embodiments, comparison parameters are a plurality of ranges of values, for example, the temperature of the patient is from about 37.9 Celsius to about 38.5 Celsius, or from about 38.6 Celsius to about 39.5 Celsius. In some embodiments, comparison parameters are a certain parameter that must be achieved, for example, the temperature of the patient is higher than 38 Celsius. In some embodiments, comparison parameters can be a combination of ranges and specific parameters, for example, the temperature of the patient is from about 37.9 Celsius to about 38.5 Celsius, or from about 38.6 Celsius to about 39.5 Celsius, or higher than 39.5.

In some embodiments, when the comparison of the data received from the assessment of the patient and the data located in the database falls either between the predetermined range/ranges or falls below or above a predetermined value, the system amends the pharmaceutical dispensing regime accordingly 412. In some embodiments, the database comprises the required information to correctly amend the pharmaceutical dispensing regime. In some embodiments, the information required to correctly amend the pharmaceutical dispensing regime is provided by the doctor and/or the personnel. Optionally, the information is provided by the doctor and/or personnel a priori. In some embodiments, the information required to correctly amend the pharmaceutical dispensing regime is recovered from past cases. In some embodiments, the information required to correctly amend the pharmaceutical dispensing regime is a combination of the above, for example, the system recovers information on how to amend the pharmaceutical dispensing regime and then transmit the information to the doctor and/or personnel for approval (see below for more information on this).

In some embodiments, after the pharmaceutical dispensing regime has been amended accordingly, the system continues to dispense the pharmaceuticals according to the regime 414. Lastly, the system updates the database 416 with the information regarding the patient, the data from the assessment and the amendment on the pharmaceutical regime, to be used later on, for the monitoring of the patient and/or for use as reference for future cases.

Exemplary Detailed Pharmaceutical Dispensing Method

FIGS. 5-11 illustrate a dynamic pharmaceutical dispensing method 500 describing a plurality of actions made by the hardware/software of the pharmaceutical dispensing system and/or the personnel and/or the patients. Also, describing a plurality of interactions and between the hardware/software of the pharmaceutical dispensing system and/or the personnel and/or the patients, according to some embodiments of the present invention.

Activation of Pharmaceutical Dispensing Method

Activation by Scheduling 502

Figure 5:
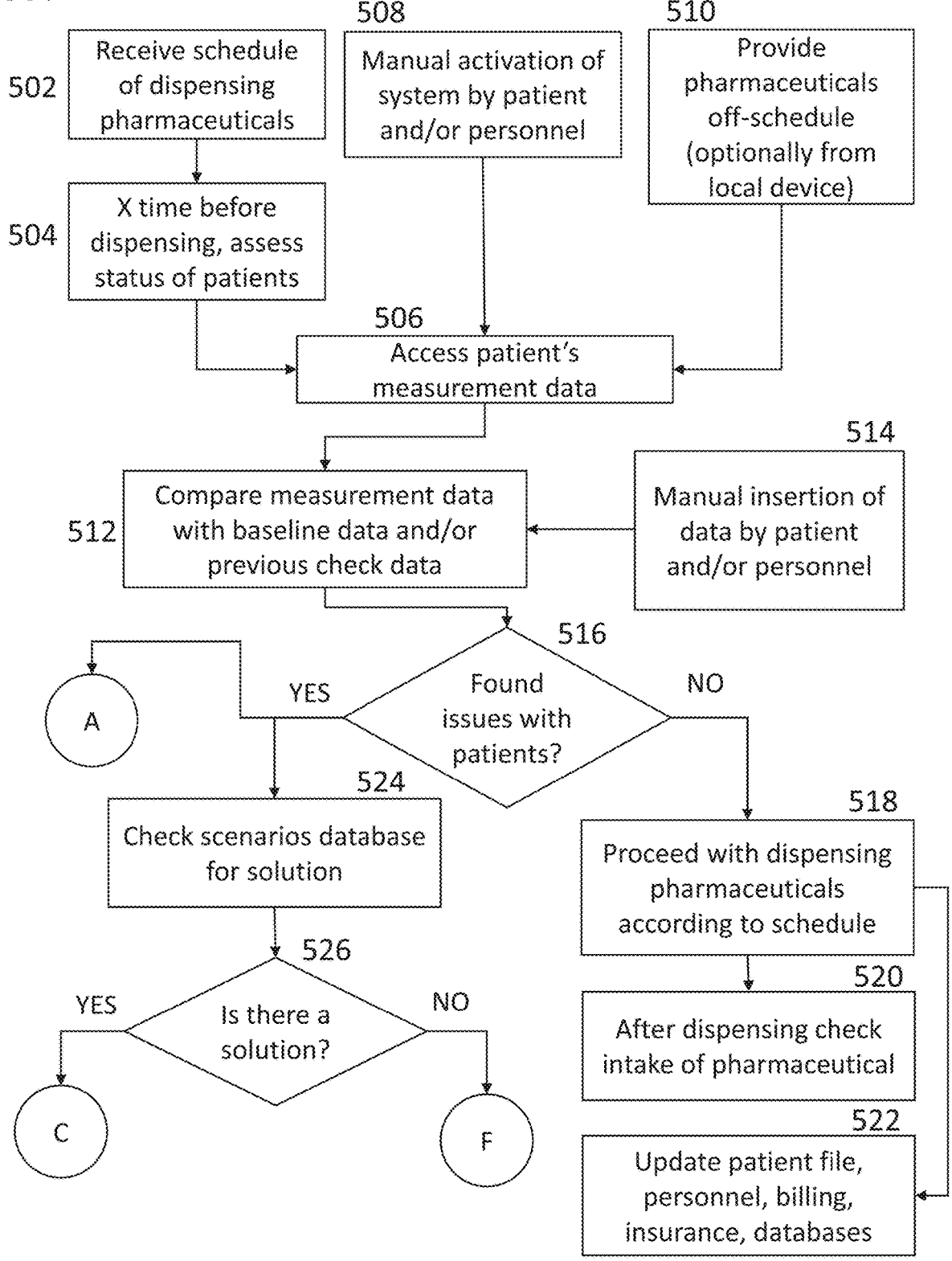
FIGS. 5, 6, 7, 8, 9, 10 and 11 are a schematic flowchart, divided in several figures, of a pharmaceutical dispensing method, according to some embodiments of the present invention.
Figure 6:
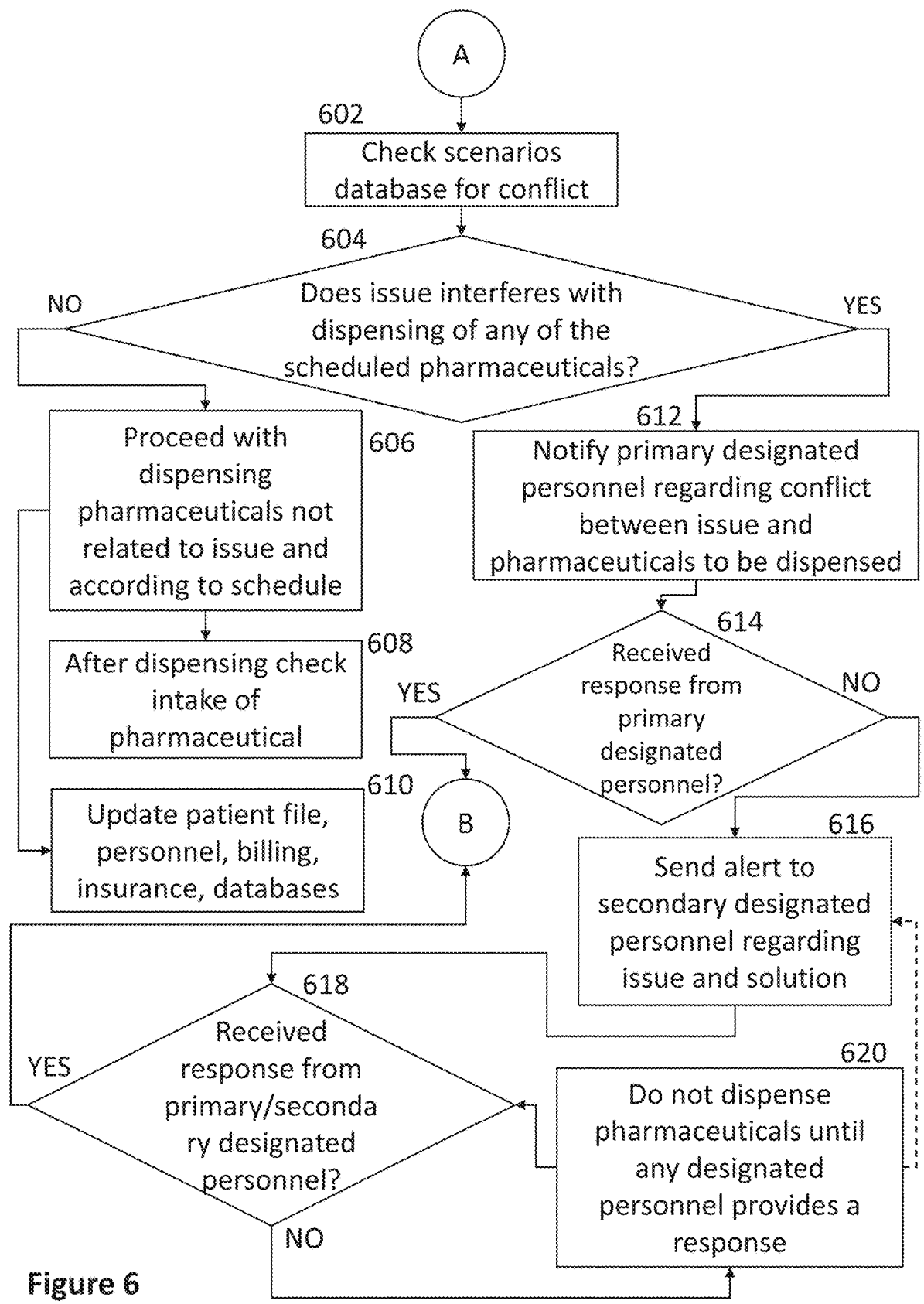
Figure 7:
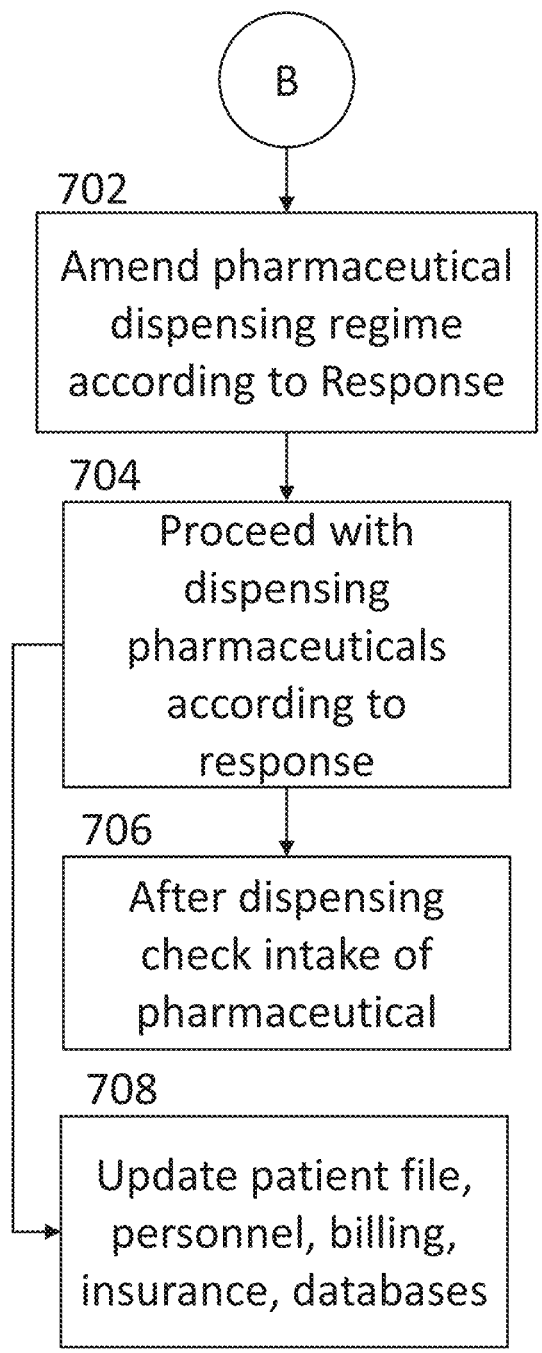
Figure 8:
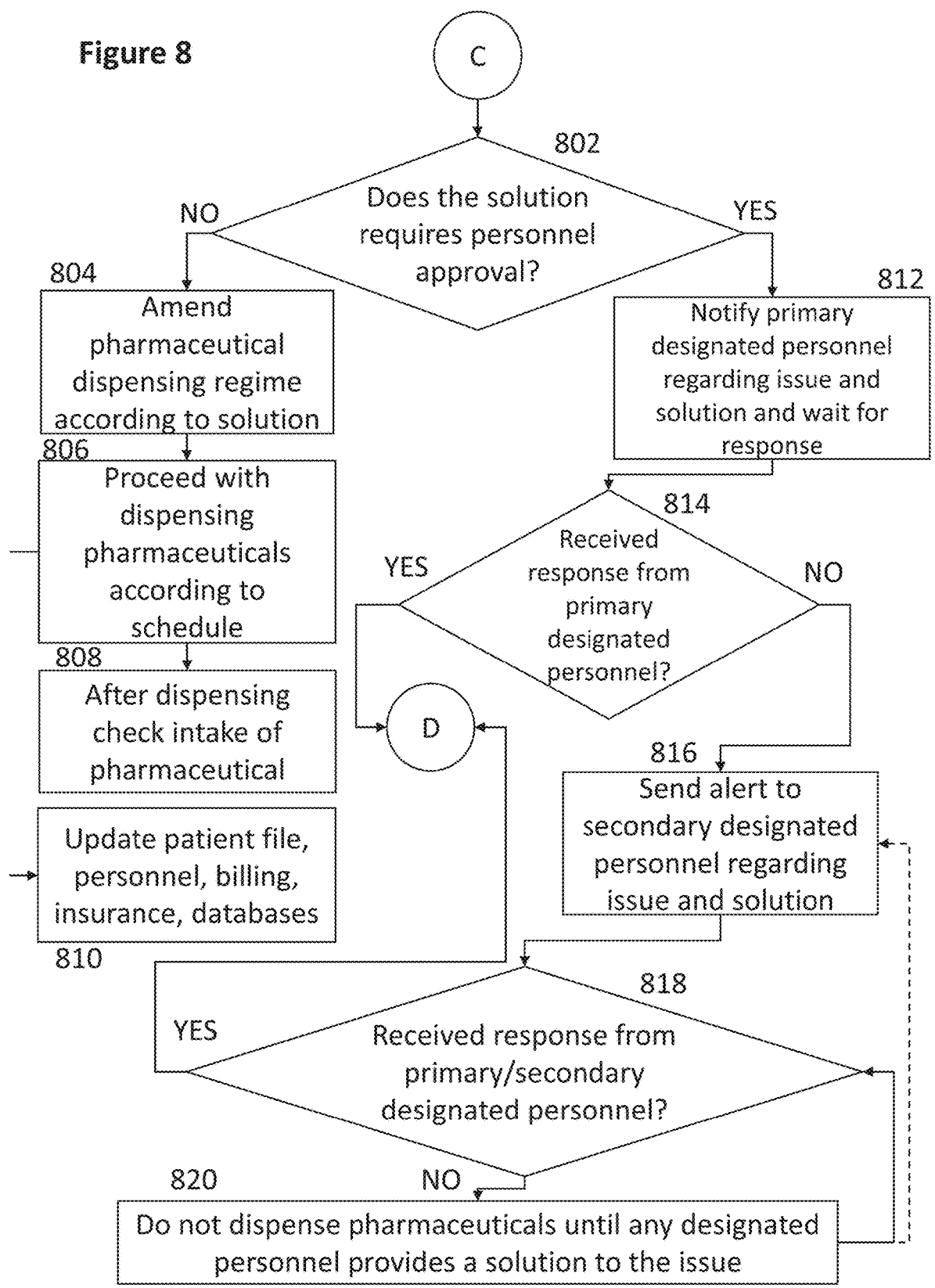
Figure 9:
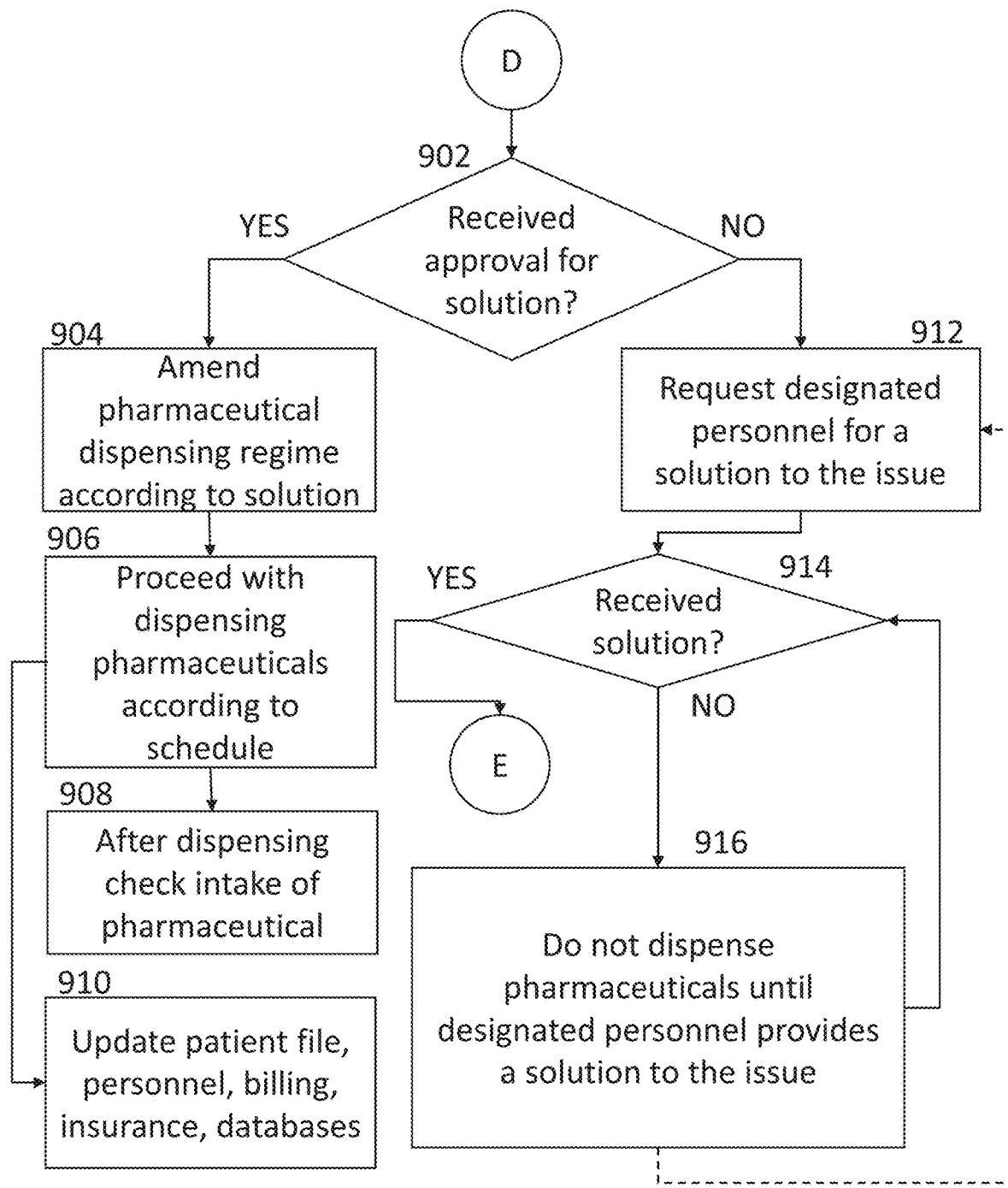
Figure 10:
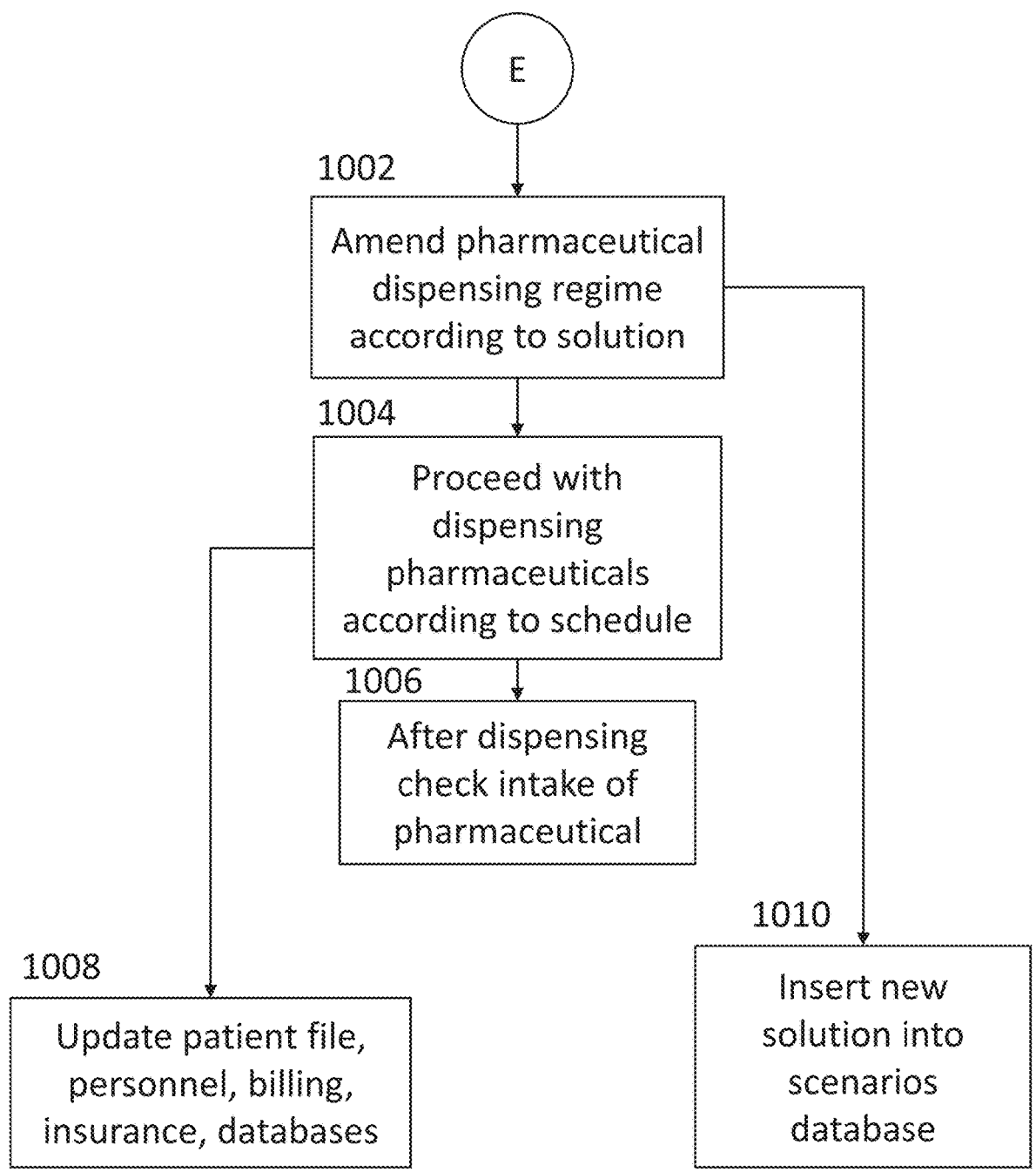
Figure 11:
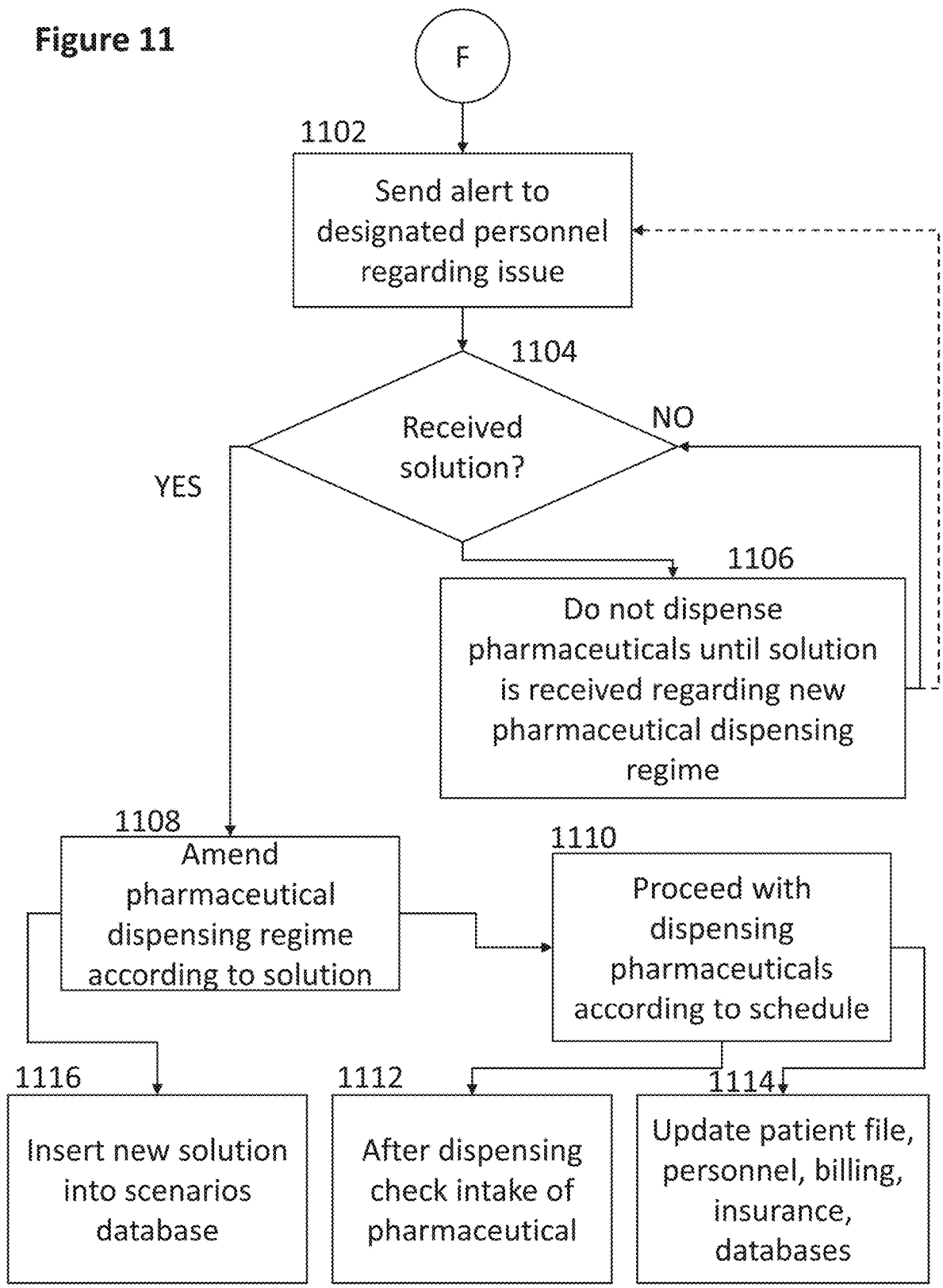

Referring now to FIG. 5, in some embodiments, the pharmaceutical dispensing system can be activated by different events, for example, the pharmaceutical dispensing system is activated after the server 104 receives a schedule of when the pharmaceutical should be dispensed 502 to the different patients. In some embodiments, the schedule is received by the doctor and/or a centralized server and/or any other entity having the privileges to provide and/or amend a pharmaceutical regime. In some embodiments, at a predetermined time before the scheduled time of dispensing the pharmaceuticals, the pharmaceutical dispensing system (software) initiates the assessment of the status of the patient 504. In some embodiments, assessment of the status of the patient is performed by accessing and utilizing measurement data collected from a plurality of sensors and measuring devices 106.

In some embodiments, the predetermined time before the scheduled time of dispensing is set manually by the personnel. In some embodiments, the predetermined time before the scheduled time of dispensing is set automatically by the pharmaceutical dispensing system taking under consideration the expected time that will require to finish all the necessary measurements. In some embodiments, to any predetermined time, a further time window is added to allow the system to perform corrective pharmaceutical dispensing actions before the scheduled time of dispensing. For example, if the estimated time to prepare and dispense the scheduled pharmaceuticals is two hours, then the software automatically adds, for example, 30 minutes to allow the system to perform corrective pharmaceutical dispensing actions. In some embodiments, corrective pharmaceutical dispensing actions may comprise requesting information from personnel, awaiting a response to an inquiry, and/or others.

In some embodiments, the pharmaceutical assessment unit is located within said pharmaceutical dispensing machine. In some embodiments, the pharmaceutical assessment unit is located outside said pharmaceutical dispensing machine. In some embodiments, the pharmaceutical assessment unit is located at a remote location and in direct communication with said pharmaceutical dispensing machine.

Collection of Data Measurements

As stated above, in some embodiments, the methods are directed to assessing pharmaceutical dispensing regimes for subjects according to the physiological status of the subject prior to commencing the pharmaceutical dispensing process. In some embodiments, one or more patient assessment units are employed to perform various actions described in more detail below.

As used herein, the terms "physiological information" or "physiological states" or "patient state" may refer to aspects of the subject physiological status that are collected either manually and/or automatically and are optionally reviewed and assessed by dedicated personnel. Accordingly, in some embodiments, dedicated personnel is qualified to review and assess physiological information of the subject.

As used herein, the term "assessment data" or "status information" refers to the data or information related to an assessment of a physiological state collected in the subject. In some embodiments, assessment data is collected in real-time, optionally while one or more dedicated personnel monitors the subject, or assessment data is compiled post hoc based on collected physiological states.

What is Measured

In some embodiments, assessing the physiological status of the patient includes, for example, measurement of temperature, blood pressure, heart rate, heart rhythm, blood sugar, a variety and concentration of a blood component, body weight, body activity, patient movements, and/or patients habits since last check, food intake, type of food that is consumed, sleep information since last check and previous pharmaceutical intake. In some embodiments, assessing the physiological status of the patient can also include the levels of a drug in the blood of the patient. In some embodiments, optimal and/or desired and/or expected drug levels are set with a set range. In some embodiments, based on the drug level found in the blood, the nurse (or any other authorized personnel) can amend the drug dose to try to achieve the set range.

In some embodiments, the drug levels in the blood can be measured by an implant sensor or an external sensor that measure these levels using spectroscopic means. In some embodiments, the measured levels information can automatically be transferred to the pharmaceutical dispensing system, which, after the assessment process, will activate the pharmaceutical dispensing machine to dispense the needed drugs dose to try to bring and/or keep the drugs levels in the blood within the set range.

Typical drugs that are monitored can be Antibiotics, Anti coagulation, Epileptic drugs, and/or Psychiatric drugs.

In some embodiments, the measurements are performed by a patient assessment units. In some embodiments, the measurements are performed manually by dedicated personnel and the data is then inserted manually into the system. In some embodiments, the patient is also allowed to insert physiological data into the system.

In some embodiments, which assessments are to be performed is decided by at least one selected from the group consisting of: previous assessments performed; manual assessment inserted by at least one authorized personnel, automatically inserted assessments by the system from historical data; any combination thereof.

When is Measured

In some embodiments, measurement data is collected at specific times during the day. In some embodiments, measurement data is performed continuously during the whole day and night. In some embodiments, measurement data is collected manually by personnel and/or the patient.

How is Measured

In some embodiments, the measurements are performed by a patient assessment units. In some embodiments, patient assessment units may collect status data of the patient that includes physiological information associated with one or more physiological states of said patient. In some embodiments, patient assessment units comprise a plurality of sensors and measurement devices are provided near the physical location of the patient. In some embodiments, sensors and/or measuring devices are located on the patient in the form of wearables and/or implants. In some embodiments, sensors and/or measuring devices are located in dedicated devices located in close proximity of the patient, for example, near the patient's bed, in the room of the room of the patient. In some embodiments, sensors and/or measuring devices are located in the furniture that the patient uses, for example, the bed, the wheelchair, a chair, or other furniture used by the patient. In some embodiments, examples of sensors and/or measuring devices are: Thermometer, Weight meter, Blood pressure sensor, Sleep sensor, Movement sensor, Cardiac activity sensor (like ECG device), Neuro activity sensor (like EEG device), Muscle activity sensor (like EMG device), Breathing sensor (like Spiroscope), Blood test sensor—invasive and/or external, Acoustical sensor (such as statoscope), Imaging sensor for detection of Ear or Throat infections, Epileptic seizure sensor, gastro-intestinal swallowed sensor, a swallowed sensor comprising a plurality of sensors in it, for example a pill comprising a plurality of sensors (like a camera, temperature sensors, movement sensor, etc.).

In some embodiments, sensors included in the system are:

Implantable sensors: Subcutaneous sensors that measure vital signs like: ECG, movement and blood chemistry like sugar levels and body temperature. An example for such device can be Reveal by Medtronic that is used for long term cardiac holter. Intravascular sensor that are placed in the blood stream and measure blood chemistry and blood flow. Swallow sensor that can be used for monitoring the GI tract.

Wearable sensors: Devices for measuring electrical parameters such as ECG, EMG and EEG. These devices usually have electrodes attached to the skin. An example for such device can be a wearable holter device. Wearable body chemistry sensors, that can measure blood and tissue chemistry, like sugar level. Limb sensors, typically placed at the patient wrist. Such devices typically measure heart rate, blood pressure, temperature and movements. In clothes sensors. For example, in the shoe sensor that measure posture, weight, movement, number of steps. Alternatively, such sensor can be placed inside textile. An example for such device can be Healthwatch wearable shirt.

Near the bed sensors: Under the mattress sensor that can measure heart rate respiration, movement, sleep status. Near the bed monitors, like blood pressure, body temperature, SPO2, ECG, body chemistry like sugar level, etc.

Facility sensors: Visual/acoustical sensors that monitor movement in the facility.

In some embodiments, the system further comprises a medication administration sensor that validates that the patient received the medication that was dispensed by the pharmaceutical dispensing machine to the nurse and then to the patient. In some embodiments, this information is used as a validation step for the next round of pharmaceutical dispensing process. In some embodiments, this information is used to also inform a family member, who is in a remote location, that the patient is being taken care of, which can potentially provide peace of mind to the family member that the patient received their medication and is compliant.

In some embodiments, further sensors are optical sensors that track movement and patient behavior, alternatively, sensors can be acoustical sensor that track patients sound such as coughing, taking, walking, sneezing and more. In some embodiments, at least one or any combination of the above are used. In some embodiments, sensors and/or measuring devices deliver the data either directly to the server 104 or to a specialized device located near the patient, for example, a data collection device (e.g. PDA, smartphone, tablet, ect.), that then delivers the collected data to the server 104.

In some embodiments, the patient assessment units comprise dedicated software to employ one or more classifiers to classify the status data of the patient to determine one or more occurrences of one or more current physiological states of the status data of patient and classify assessment data to determine one or more scores that are associated with one or more current physiological states included in the one or more physiological states of the patient, such that the assessment data includes information associated with one or more current physiological states of the one or more physiological states of the patient.

In some embodiments, the analysis of the data is performed at the server and not at the patient assessment unit. In some embodiments, the analysis is performed by both the patient assessment unit and the server.

In some embodiments, the data is compared to the same patient historical data to identify trend of development of new pathology and to the other members of the facility to identify, for example, an onset of epidemic or inter-facility infection.

Activation by Manual Activation by the Patient/Personnel 508

In some embodiments, another event that activates the pharmaceutical dispensing method can be a manual activation 508 by the patient 108 and/or personnel 110. For example, if the patient complains that he is not feeling well, the patient may activate the system to perform a new collection of measurements data to be used later on by the personnel 110. Another example, the personnel 110 may activate the system manually to access the patient's measurement data 506 or to perform a new collection of measurements data in order to perform and/or request further pharmaceutical dispensing actions.

In some embodiments, the dedicated personnel have a dedicated personnel's device, which is connected to the system. In some embodiments, the dedicated personnel may activate the patient's assessment unit remotely using the dedicated personnel's device.

Activation by Manual Activation by the Personnel to Provide Off-Schedule Dispensing of Pharmaceuticals 510

In some embodiments, another event that activates the pharmaceutical dispensing system can be a manual activation 510 by personnel 110 to provide the patient 108 with an unscheduled pharmaceutical. For example, if the patient 108 complains of a headache, the personnel 110 can access the system to request the at least one pharmaceutical dispensing machine 102 to provide a pharmaceutical. Optionally, the at least one pharmaceutical dispensing machine is a small pharmaceutical dispensing machine located in the same floor as the patient's room.

Comparing Patient's Measurement Data with Other Data 512

In some embodiments, after the data of the measurements is collected, the data is then compared to a baseline data and/or to a previous measured data of the patient 512. In some embodiments, baseline data also includes: prescribed drugs, medical history, similar cases in the past and history of measurement activations, for example, if the patient has a history of complains.

In some embodiments, all past and current information regarding the patients are used for comparison and alert purposes, for example, in the case of an abnormal number of cases influenza or digestion problems, might indicate an epidemic or due to bad food.

In some embodiments, the server 104 is operative to receive status data of the patients from the patient assessment unit or the dedicated personnel's device to enable the assessment tool software to classify the data as positive, neutral, or negative—thereby generating classification results—, aggregate the classification results, and store the classification results on a metadata store. In some embodiments, the patient assessment unit is arranged to collect status data that may later or in real-time be provided to the server and the assessment tool software. In some embodiments, the server and the assessment tool software may, additionally or alternatively, be operative to classify the status data to identify pertinent events in the course of the collection of the physiological state of the patient. For example, an increase in the temperature of the patient, an adverse reaction, a change in the lab blood results and the like may be identified.

In some embodiments, the server and the assessment tool software then process, make available, and act on the classification information. For example, the server and the assessment tool software may process aggregate classification information (including classification information retrieved from metadata store), to identify trends, patterns, exceptions, or correlations or relationships to other data (e.g. which data elements most influence pharmaceutical performance and/or patient outcomes). In some embodiments, the server and the assessment tool software may make this information available through, for example, a website, allowing access to relevant portions of physiological status of the patient received from the patient assessment unit or the dedicated personnel's device, insights realized by direct classification of the physiological data, or comparisons to other data elements, including those pertaining to other patients or physiological states of the same patient. Furthermore, in some embodiments, the patient assessment unit or the dedicated personnel's device is integrated with a scheduling system to help assign future tasks and/or modify future pharmaceutical dispensing regimes.

In some embodiments, physiological data may include data that documents a subject's physiological state, such as body temperature, blood lab results, sleep patterns, blood pressure and the like. In some embodiments, classifications include an output of a machine learning algorithm applied to the physiological data. Additionally or alternatively, classifications include an output of a machine learning algorithm applied to manually inserted physiological data inserted by dedicated personnel. In some embodiments, aggregate classification results include the result of an analysis applied to classification results. For example, in the context of providing a particular medicine to a subject, aggregate classification results may include when the particular medicine was first taken, what are the intervals that the certain medicine needs to be taken, possible adverse effects of the medicine, contraindications of the medicine, etc. In some embodiments, classification results associated with multiple subjects over multiple cases are contemplated, allowing comparison between subjects, advancement or regression in the physiological state of a given subject, or the like, to be reviewed.

Manual Insertion of Measurement Data 514

In some embodiments, measurement data is inserted manually 514 by the personnel 110 and/or the patient 108. For example, the temperature of the patient was taken using a device that is not connected to the server/data collection device, the data is inserted manually and then used by the system.

In some embodiments, physiological statuses are updated via a dedicated personnel's device. In some embodiments, dedicated personnel's devices are enabled to communicate (e.g., via a Bluetooth or other wireless technology, or via a USB cable or other wired technology) with at least one patient assessment unit. In some embodiments, at least some of dedicated personnel's devices operate over a wired and/or wireless network, to communicate with other dedicated personnel's devices and/or the server 104.

In some embodiments, a dedicated personnel's device is included in a system to be operated by a dedicated personnel, such as that shown in FIG. 1. In some embodiments, the dedicated personnel's device may be a mobile device (e.g., a smart phone or tablet), a stationary/desktop computer, or the like. In some embodiments, the dedicated personnel's device may include processor, such as a central processing unit (CPU), in communication with memory via bus. In some embodiments, the dedicated personnel's device may also include a power supply, a network interface, a processor-readable stationary storage device, a processor-readable removable storage device, an input/output interface, camera (s), video interface, touch interface, a display, a keypad, a global positioning systems (GPS) receiver, or the like. In some embodiments, the dedicated personnel's device may optionally communicate with a base station (not shown), or directly with the server.

In some embodiments, the dedicated personnel's device is configured to enable a user to log into an account and/or user interface to access/view content data. In some embodiments, a browser may enable a user to view reports of assessment data that is generated by the server. In some embodiments, the browser/user interface may enable the user to customize a view of the report and to receive prescriptive recommendations for amending the pharmaceutical regime based upon their assessment data. In some embodiments, as described herein, the extent to which a user can customize the reports may depend on permissions/restrictions for that particular user.

Assessment of Issues 516

In some embodiments, the server 104 is operative to receive status data of the patients from the patient assessment unit or the dedicated personnel's device to enable the assessment tool software to classify the data as positive, neutral, or negative, aggregate the classification results, and store the classification results on a metadata store. In some embodiments, the patient assessment unit is arranged to collect status data that may later or in real-time be provided to the server and the assessment tool software. In some embodiments, the server and the assessment tool software may, additionally or alternatively, be operative to classify the status data to identify pertinent events in the course of the collection of the physiological state of the patient. For example, an increase in the temperature of the patient, an adverse reaction, a change in the lab blood results and the like may be identified.

In some embodiments, the server and the assessment tool software then process, make available, and act on the classification information. For example, the server and the assessment tool software may process aggregate classification information (including classification information retrieved from metadata store), to identify trends, patterns, exceptions, or correlations or relationships to other data (e.g. which data elements most influence pharmaceutical performance and/or patient outcomes). In some embodiments, the server and the assessment tool software may make this information available through, for example, a website, allowing access to relevant portions of physiological status of the patient received from the patient assessment unit or the dedicated personnel's device, insights realized by direct classification of the physiological data, or comparisons to other data elements, including those pertaining to other patients or physiological states of the same patient. Furthermore, in some embodiments, the patient assessment unit or the dedicated personnel's device is integrated with a scheduling system to help assign future tasks and/or modify future pharmaceutical dispensing regimes.

In some embodiments, classifiers are used to determine one or more scores associated with one or more physiological states included in the one or more physiological states of said patient. In some embodiments, the scores are also associated with one or more pharmaceuticals. In some embodiments, the scores are also associated with one or more diseases, symptoms, treatments related to symptoms, sleep patterns, psychological states, etc. In some embodiments, the scores are also associated with one or more pharmaceutical dispensing regimes related to one or more pathologies.

In some embodiments, scores are used to perform one or more correlations. In some embodiments, providing the one or more correlation values associated with the one or more physiological states of said patient may include: receiving current physiological status of the patient that comprises one or more current physiological data; correlating the current physiological status with at least one physiological status (e.g.: previous measured physiological status, desired physiological status, historical status data content, assessment data, scores); modifying the one or more classifiers based on the correlation of the current physiological status with at least one physiological status (e.g.: previous measured physiological status, desired physiological status, historical status data content, assessment data, scores).

In some embodiments, classifying the assessment data may include: classifying physiological data that is provided by different sources (e.g. literature, manual insertions by dedicated personnel, previous measurements from the patient); and further determining the one or more scores based on the classification of the physiological data.

In some embodiments, the patient assessment units and/or assessment tool software in the server provide one or more correlation values associated with the one or more physiological states of said patient based on historical status data of patient, assessment data, and scores.

In some embodiments, the patient assessment unit and/or assessment tool software in the server provide a report that includes a localized evaluation of the one or more physiological states of said patient based on the correlation values, status data of patient, assessment data, and scores.

In some embodiments, the patient assessment unit and/or assessment tool software in the server provide real-time feedback to one or more subjects from which status data is being collected. Accordingly, one or more responses from the one or more subjects that are associated with the real-time feedback may be collected.

In some embodiments, the patient assessment unit and/or assessment tool software in the server are arranged to update the one or more classifiers based on the one or more correlation values.

In some embodiments, the patient assessment unit and/or assessment tool software in the server are arranged to extract a portion of the status data of patient associated with the assessment data based on the one or more scores that exceed a defined value. Accordingly, the patient assessment unit and/or assessment tool software in the server are arranged to provide the extracted portion of the status data of patient and its assessment data to a classification processing engine in a dedicated server for use as training data.

In some embodiments, the result of the comparison of the data may indicate an issue and/or problem with the patient. In some embodiments, predetermined values and/or a range of predetermined values are provided in order to differentiate between a "normal" value of measurement and an "abnormal" value of measurement. In some embodiments, the measured data is compared with the predetermined values and/or a range of predetermined values in order to decide whether the measured data is either "normal" or "abnormal".

In some embodiments, predetermined values are values related to the specific patient. Optionally, predetermined values are measured before the patients begins a pharmaceutical regimen and said values are then used as baseline for the following measurements. In some embodiments, predetermined values are average values collected from a plurality of patients (either healthy and/or sick) over a period of time. In some embodiments, predetermined values are set by the doctor and/or the personnel.

Response to Assessment of Issues—No Issues

In some embodiments, when the result of the comparison indicates that there are no issues with the patient, the system continues with the scheduled dispensing of the pharmaceuticals 518. In some embodiments, the system is further adapted to perform compliance actions regarding the intake of the pharmaceuticals by the patient 520. In some embodiments, after the dispensing of pharmaceuticals, the system optionally updates 522 the patient's file, the personnel, the billing department, the insurance companies, the databases and/or any other system and/or department that requires updating.

Scenarios Database

Before describing the responses of the pharmaceutical dispensing system to issues, a description of the "scenarios database" is required. In some embodiments, the system comprises a "scenarios database", which comprises data regarding cases related to sicknesses and what to do, with respect to the pharmaceutical dispensing regime, in case the status of the patient changes. In some embodiments, the "scenarios database" comprises data from scientific literature, past cases, manual insertion of data, and any other source of data related to what to do in any specific case.

In some embodiments, an example of the process of use of the scenarios database is as follows:

Periodically, a physician reviews the user/patient condition and provides drugs prescription orders (as shown in FIG. 12), both for routine drugs and "PRN" (up on request) drugs. For example, the routine drugs can be drugs that manage blood pressure or cholesterol levels. In some embodiments, the orders for the 'on demand' drugs include orders like: "if the user temperature is above set value, provide him with a drug to reduce fever". "If the patient suffers from pain, provide him with pain killer drug". In some embodiments, the orders can also include instructions on the time of delivery of the drug. If a user/patient suffers from insomnia, for example, the patient should get a drug to help him sleep. In some embodiments, the timing of the drug intake vary from patient to patient. In some embodiments, a sleep sensor is used to determine the typical time of sleep of the patient and the pharmaceutical dispensing machine will provide the needed drug at the typical sleep time for each specific patient.

Response to Assessment of Issues—Yes Issues

In some embodiments, when the result of the comparison indicates that there are issues with the patient because of the result of the comparison showed the measured is either higher or lower than the predetermined values and/or a range of predetermined values, the software of the pharmaceutical dispensing system performs at least two distinct actions:

1. Check Conflict with Pharmaceuticals to be Dispensed

In some embodiments, (following the letter A to FIG. 6) the system accesses the "scenarios database" 602 in order to assess if the issue interferes with the dispensing of any of the scheduled pharmaceuticals 604.

In some embodiments, when there is no conflict between the issue and any or some of the scheduled pharmaceuticals to be dispensed, the system proceeds with the dispensing of the pharmaceuticals that are not in conflict with the issue 606. In some embodiments, the system is further adapted to perform compliance actions regarding the intake of the pharmaceuticals by the patient 608. In some embodiments, after the dispensing of pharmaceuticals, the system optionally updates 610 the patient's file, the personnel, the billing department, the insurance companies, the databases and/or any other system and/or department that requires updating.

In some embodiments, when there is a conflict between the issue and all or some of the scheduled pharmaceuticals to be dispensed, the system proceeds with notifying a primary designated personnel regarding the conflict between the issue and the pharmaceuticals to be dispensed 612. In some embodiments, the system then assesses if a response from the primary designated personnel has been received 614. If a response from the primary designated personnel has been received, then (following the letter B to FIG. 7) the system amends the pharmaceutical dispensing regime according to the response received by the personnel 702. In some embodiments, the system then proceeds with the dispensing of the pharmaceuticals according to the response 704. In some embodiments, the system is further adapted to perform compliance actions regarding the intake of the pharmaceuticals by the patient 706. In some embodiments, after the dispensing of pharmaceuticals, the system optionally updates 708 the patient's file, the personnel, the billing department, the insurance companies, the databases and/or any other system and/or department that requires updating.

Returning to FIG. 6, if no response has been received from the primary designated personnel, then the system sends an alert to a secondary designated personnel 616. In some embodiments, the system then assesses if a response from the primary and/or secondary designated personnel has been received 618. If no response has been received from either the primary or the secondary designated personnel, then the system does not dispense pharmaceuticals until any designated personnel provides a response 620, while in parallel continues to send alerts to all designated personnel (dashed arrow). If a response from the primary or secondary designated personnel has been received, then (following the letter B to FIG. 4) the system amends the pharmaceutical dispensing regime according to the response received by the personnel 402, as explained above.

Returning to FIG. 2, the other action taken by the software of the pharmaceutical dispensing system is:
2. Check Solution to the Issue In some embodiments, the system accesses the "scenarios database" in order to search for a solution to the issue 224. In some embodiments, the system assesses if there is a solution to the issue 226.

In some embodiments, if there is a solution, then (following the letter C to FIG. 8) the systems assesses if the solution requires personnel approval to be executed 802. In some embodiments, if the solution does not require the approval of the personnel, then the system amends the pharmaceutical dispensing regime according to the solution 804. In some embodiments, the system then proceeds with the dispensing of the pharmaceuticals according to the schedule 806. In some embodiments, the system is further adapted to perform compliance actions regarding the intake of the pharmaceuticals by the patient 808. In some embodiments, after the dispensing of pharmaceuticals, the system optionally updates 810 the patient's file, the personnel, the billing department, the insurance companies, the databases and/or any other system and/or department that requires updating.

In some embodiments, if the solution does require the approval of the personnel, then the system proceeds with notifying a primary designated personnel regarding the issue found with the patient and the solution found in the "scenarios database" 812. In some embodiments, the system then assesses if a response from the primary designated personnel has been received 814. If a response from the primary designated personnel has been received, then (following the letter D to FIG. 9) the system assesses if the response comprises approval of the solution 902. In some embodiments, if the response does comprise an approval to the solution then the system amends the pharmaceutical dispensing regime according to the solution 904. In some embodiments, the system then proceeds with the dispensing of the pharmaceuticals according to the solution and according to schedule 906. In some embodiments, the system is further adapted to perform compliance actions regarding the intake of the pharmaceuticals by the patient 908. In some embodiments, after the dispensing of pharmaceuticals, the system optionally updates 910 the patient's file, the personnel, the billing department, the insurance companies, the databases and/or any other system and/or department that requires updating.

In some embodiments, if the response does not comprise an approval to the solution then the system requests from the designated personnel to provide a solution to the issue 912. In some embodiments, the system then assesses if a solution has been received from the designated personnel 914. If no response has been received from the designated personnel, then the system does not dispense pharmaceuticals until any designated personnel provides a response 916, while in parallel continues to send alerts to all designated personnel (dashed arrow). If a response from the designated personnel has been received, then (following the letter E to FIG. 10) the system amends the pharmaceutical dispensing regime according to the solution received by the personnel 1002. In some embodiments, the system then proceeds with the dispensing of the pharmaceuticals according to the solution and according to the schedule 1004. In some embodiments, the system is further adapted to perform compliance actions regarding the intake of the pharmaceuticals by the patient 1006. In some embodiments, after the dispensing of pharmaceuticals, the system optionally updates 1008 the patient's file, the personnel, the billing department, the insurance companies, the databases and/or any other system and/or department that requires updating. In some embodiments, in addition, the system inserts the new solution provided by the designated personnel to the "scenarios database" 1010.

Returning to FIG. 8, if no response has been received from the primary designated personnel, then the system sends an alert to a secondary designated personnel 816. In some embodiments, the system then assesses if a solution from the primary and/or secondary designated personnel has been received 818. If no solution has been received from either the primary or the secondary designated personnel, then the system does not dispense pharmaceuticals until any designated personnel provides a solution 820, while in parallel continues to send alerts to all designated personnel (dashed arrow). If a solution from the primary or secondary designated personnel has been received, then (following the letter D to FIG. 9) the system assesses if the response comprises approval of the solution 902, as explained above.

Returning to FIG. 2, in some embodiments, if there is no solution in the scenarios database, then (following the letter F to FIG. 11) the system requests from the designated personnel to provide a solution to the issue 1102. In some embodiments, the system then assesses if a solution has been received from the designated personnel 1104. If no response has been received from the designated personnel, then the system does not dispense pharmaceuticals until any designated personnel provides a response 1106, while in parallel continues to send alerts to all designated personnel (dashed arrow). If a response from the designated personnel has been received, then the system amends the pharmaceutical dispensing regime according to the solution received by the personnel 1108. In some embodiments, the system then proceeds with the dispensing of the pharmaceuticals according to the solution and according to the schedule 1110. In some embodiments, the system is further adapted to perform compliance actions regarding the intake of the pharmaceuticals by the patient 1112. In some embodiments, after the dispensing of pharmaceuticals, the system optionally updates 1114 the patient's file, the personnel, the billing department, the insurance companies, the databases and/or any other system and/or department that requires updating. In some embodiments, in addition, the system inserts the new solution provided by the designated personnel to the "scenarios database" 1116.

It is expected that during the life of a patent maturing from this application many relevant diagnostic methods, communication methods, monitoring devices, pharmaceutical treatment methods and pharmaceutical dispensing methods will be developed; the scope of the terms scenarios, monitoring, communicating, pharmaceutical dispensing methods and pharmaceutical treatment methods are intended to include all such new technologies a priori.

As used herein with reference to quantity or value, the term "about" means "within ±20% of".

The terms "issue", "issues", "problem" and "problems" are interchangeable in their meaning.

The terms "comprises", "comprising", "includes", "including", "has", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular forms "a", "an" and "the" include plural references unless the context clearly dictates otherwise.

Throughout this application, embodiments of this invention may be presented with reference to a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as "from 1 to 6" should be considered to have specifically disclosed subranges such as "from 1 to 3", "from 1 to 4", "from 1 to 5", "from 2 to 4", "from 2 to 6", "from 3 to 6", etc.; as well as individual numbers within that range, for example, 1, 2, 3, 4, 5, and 6. This applies regardless of the breadth of the range.

Whenever a numerical range is indicated herein (for example "10-15", "10 to 15", or any pair of numbers linked by these another such range indication), it is meant to include any number (fractional or integral) within the indicated range limits, including the range limits, unless the context clearly dictates otherwise. The phrases "range/ranging/ranges between" a first indicate number and a second indicate number and "range/ranging/ranges from" a first indicate number "to", "up to", "until" or "through" (or another such range-indicating term) a second indicate number are used herein interchangeably and are meant to include the first and second indicated numbers and all the fractional and integral numbers therebetween.

Unless otherwise indicated, numbers used herein and any number ranges based thereon are approximations within the accuracy of reasonable measurement and rounding errors as understood by persons skilled in the art As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

EXAMPLES

Reference is now made to the following examples, which together with the above descriptions illustrate some embodiments of the invention in a non limiting fashion.

Example 1

A case where a patient suffers from Parkinson as medical a condition. Several sensors including movement sensor, sleep sensor, bed activity sensor, monitor the patient. Based on his movement activity and/or sleep status and/or sleeping patterns and/or time of getting out of bed, the system automatically prescribes the needed dose of Levadopa or/and Carbidopa for its optimal treatment, according to previous treatments of the patient and following the physician's instructions. The system activates the pharmaceutical dispensing machine that prepares and dispenses the pharmaceuticals.

Example 2

A case where a patient reports suffering from diarrhea/headache/constipation/sleep problem/vaginal infection/urinary infection, stomach ache or muscle pains. The system identifies the best drug for the needed treatment according to the specific patient, taking into consideration his medical history and the physician recommendation for the treatment of specific conditions. The system activates the pharmaceutical dispensing machine that prepares and dispenses the pharmaceuticals.

Example 3

In a case where several patients in the same facility are diagnosed as having bacterial influenza, the system is configured to connect the different cases to diagnose a possible epidemic case in the facility. Any additional patient that will also show signs of influenza, like high body temperature and coughing, based on the sensor data collected will also be diagnosed with influenza. Furthermore, in this scenario, the system will notify the main physician of the situation. The system then dispenses the needed antibiotics for the additional patient, according to physician recommendations.

Example 4

In a case where a patient suffers from chronic high blood pressure. The patient sensors monitor on a regular basis his blood pressure level according to previous monitoring regimes and/or according to historical monitoring regimes from other cases. Based on the sensor results, the system is configured to automatically set the required dose of the drug for the treatment of blood pressure according to the real-time blood pressure information collected from the patient.

Example 5

In a case where patient underwent surgery, the patient complains on pains. The patient himself inserts into the system the information that he is in pain, and, based on the physician set of instructions, the system activates the pharmaceutical dispensing machine to dispense the needed anti-pain drug.

Example 6

In a case where a patient receives a drug treatment for a medical condition, the system monitors the patient's drug concentration in the blood using a blood test sensor. For example, typical drugs can be antibiotics, anticoagulants, epileptic drugs or psychiatric drugs. Based on the measured blood levels, the system sets the required drug dose for dispensing.

Example 7

In a case where a patient's activity while sleeping is monitored by sensors and/or by camera. The system identifies special patterns, for example rolling in bed, number of times that the patient woke up to urinate, vomiting and any abnormal behavior, compared to his historical sleeping activity. Once the system identifies the abnormal behavior, the system is configured to provide a new schedule for dispensing proper medicaments, taking into consideration his medical history and the physician recommendations for the treatment of this specific condition. Then, the system automatically activates the pharmaceutical dispensing machine, which dispenses the needed drug to the patient.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A method of managing a pharmaceutical dispensing process for a plurality of patients, the method performed by a pharmaceutical dispensing machine, the method comprising:

At an automatic pharmaceutical dispensing assessment unit in said pharmaceutical dispensing machine:
  a. receiving at least one pharmaceutical dispensing regime for each one of said plurality of patients from at least one physician; said at least one pharmaceutical dispensing regime comprising, for each of said plurality of patients, at least one pharmaceutical dispensing schedule comprising at least one pharmaceutical to be dispensed, at least one quantity of said pharmaceutical to be dispensed at said at least one time of dispensing and a prescribed time of consumption of said at least one pharmaceutical by each of said plurality of patients; b. receiving at least one time of dispensing said at least one pharmaceutical from said pharmaceutical dispensing machine in order to meet said prescribed time of consumption of said at least one pharmaceutical by each of said plurality of patients;

At a time prior to commencing the pharmaceutical dispensing process, said pharmaceutical dispensing process comprises packaging said at least one pharmaceutical for each of said plurality of patients in individual packages and for all of said plurality of patients, performing:
  i. automatically calculating a time required for said pharmaceutical dispensing machine to finish said packaging of said individual packages for all of said plurality of patients according to said at least one time of dispensing of said pharmaceutical from said pharmaceutical dispensing machine and according to said prescribed time of consumption of a respective at least one pharmaceutical by each of said plurality of patients;
  ii. automatically requesting and collecting status information of each one of said plurality of patients, including information data of at least one of physiological status, physical status and mental status of each one of said plurality of patients;
  iii. automatically comparing said status of each one of said plurality of patients with at least one reference data;
  iv. automatically assessing when said status of each one of said plurality of patients differs from said reference data; and said difference affects said at least one pharmaceutical dispensing regime;
  v. automatically amending said at least one pharmaceutical dispensing regime according to said status of each one of said plurality of patients to create at least one amended pharmaceutical dispensing regime when said difference in said status from said reference data of each one of said plurality of patients affects said at least one pharmaceutical dispensing regime;
  vi. automatically instructing said pharmaceutical dispensing machine to dispense said at least one pharmaceutical according to said at least one amended pharmaceutical dispensing regime;

wherein said (i)-(vi) are initiated at a time prior to said at least one time of dispensing said at least one pharmaceutical from said pharmaceutical dispensing machine; said time being said calculated time required for said pharmaceutical dispensing machine to finish said packaging;

At said pharmaceutical dispensing machine:
  c. performing said packaging of said at least one pharmaceutical for each one of said plurality of patients in said individual packages and for all of said plurality of patients according to said at least one amended pharmaceutical dispensing regime;
  d. dispensing by said pharmaceutical dispensing machine said individual packages according to said at least one amended pharmaceutical dispensing regime.

2. The method according to claim 1, wherein said assessing a status of each one of said plurality of patients comprises performing at least one test and said determined time before said time of dispensing is relative to the time required to receive results of said test.

3. The method according to claim 1, wherein said assessing a status of each one of said plurality of patients comprises measuring at least one physiological parameter of said patient.

4. The method according to claim 1, wherein said assessing a status of each one of said plurality of patients comprises connecting each one of said plurality of patients to at least one sensor.

5. The method according to claim 1, wherein said amending said at least one pharmaceutical dispensing regime further comprises notifying said at least one physician of said at least one amended pharmaceutical dispensing regime.

6. The method according to claim 1, wherein said assessing a status of each one of said plurality of patients comprises sending information about said assessment status to at least one server to be analyzed by an assessment tool software.

7. The method according to claim 1, wherein said assessing a status of each one of said plurality of patients further comprises revising said pharmaceutical dispensing regime to assess if said physician provided conditions on which said pharmaceutical dispensing regime needs to be amended according to a status of each one of said plurality of patients at a time from 10 minutes to 8 hours before the time of dispensing pharmaceuticals.

8. The method according to claim 1, wherein said assessing when said status of each one of said plurality of patients affects said at least one pharmaceutical dispensing regime comprises comparing one or more selected from the group consisting of: said status information with data located in a server, said status information with historical status data content, said status information with assessment data, said status information with status information from other patients in the vicinity of each one of said plurality of patients, said status information with data from scientific and medical publications, said status information with data manually inserted by the doctor and any combination thereof.

9. An automatic pharmaceutical dispensing assessment unit for a pharmaceutical dispensing system that performs at least one pharmaceutical dispensing process for a plurality of patients, the unit comprising:
   a. at least one processor device;
   b. at least one computer readable medium having computer program instructions thereon;
   c. at least one communication unit in communication with:
      i. at least one server of a pharmaceutical dispensing system; and
      ii. at least one patient assessment unit;
      iii. at least one pharmaceutical dispensing machine;
   wherein said at least one processor device in said automatic pharmaceutical dispensing assessment unit execute said program instructions to perform actions, including:
   d. receiving at least one pharmaceutical dispensing regime for each one of said plurality of patients from at least one physician; said at least one pharmaceutical dispensing regime comprising, for each of said plurality of patients, at least one pharmaceutical dispensing schedule comprising at least one pharmaceutical to be dispensed, at least one quantity of said pharmaceutical to be dispensed at said at least one time of dispensing and a prescribed time of consumption of said at least one pharmaceutical by each of said plurality of patients;
   e. receiving at least one time of dispensing said at least one pharmaceutical from said pharmaceutical dispensing machine in order to meet said prescribed time of consumption of said at least one pharmaceutical by each of said plurality of patients;

At a time prior to commencing the pharmaceutical dispensing process, said pharmaceutical dispensing process comprises packaging said at least one pharmaceutical for each of said plurality of patients in individual packages and for all of said plurality of patients, performing:
   iv. automatically calculating a time required for said pharmaceutical dispensing machine to finish said packaging of said individual packages for all of said plurality of patients according to said at least one time of dispensing of said pharmaceutical from said pharmaceutical dispensing machine and according to said prescribed time of consumption of a respective at least one pharmaceutical by each of said plurality of patients;
   v. automatically requesting and collecting status information of each one of said plurality of patients, including information data of at least one of physiological status, physical status and mental status of each one of said plurality of patients;
   vi. automatically comparing said status of each one of said plurality of patients with at least one reference data;
   vii. automatically assessing when said status of each one of said plurality patient differs from said reference data; and said difference affects said at least one pharmaceutical dispensing regime;
   viii. automatically amending said at least one pharmaceutical dispensing regime according to said status of each one of said plurality of patients to create at least one amended pharmaceutical dispensing regime when said difference in said status from said reference data of each one of said plurality of patient affects said at least one pharmaceutical dispensing regime;
   ix. automatically instructing said pharmaceutical dispensing machine to dispense said at least one pharmaceutical according to said at least one amended pharmaceutical dispensing regime;
wherein said (iv)-(ix) are initiated at a time before said at least one time of dispensing said at least one pharmaceutical from said pharmaceutical dispensing machine; said time being said calculated time required for said pharmaceutical dispensing machine to finish said packaging;

At said pharmaceutical dispensing machine:
   f. performing said packaging said at least one pharmaceutical for each one of said plurality of patients in said individual packages and for all of said plurality of patients according to said at least one amended pharmaceutical dispensing regime;
   g. dispensing by said pharmaceutical dispensing machine said individual packages according to said at least one amended pharmaceutical dispensing regime.

10. The automatic pharmaceutical dispensing assessment unit according to claim 9 wherein said automatic pharmaceutical dispensing assessment unit is located within said pharmaceutical dispensing machine.

11. The automatic pharmaceutical dispensing assessment unit according to claim 9, wherein said automatic pharmaceutical dispensing assessment unit is located outside said pharmaceutical dispensing machine.

12. The automatic pharmaceutical dispensing assessment unit according to claim 9, wherein said automatic pharmaceutical dispensing assessment unit is located at a remote location and in direct communication with said pharmaceutical dispensing machine.

13. The automatic pharmaceutical dispensing assessment unit according to claim 9, wherein said automatically assessing a status of each one of said plurality of patients comprises performing at least one test and said determined time before said time of dispensing is relative to the time required to receive results of said test.

14. The automatic pharmaceutical dispensing assessment unit according to claim 9, wherein automatically assessing a status of each one of said plurality of patients comprises measuring at least one physiological parameter of each one of said plurality of patients.

15. The automatic pharmaceutical dispensing assessment unit according to claim 9, wherein said automatically assessing a status of each one of said plurality of patients comprises connecting said patient to at least one sensor.

16. The automatic pharmaceutical dispensing assessment unit according to claim 15, wherein said automatically assessing when said status of each one of said plurality of patients affects said at least one pharmaceutical dispensing regime comprises comparing one or more selected from the group consisting of: said status information with data located in said server, said status information with historical status data content, said status information with assessment data, said status information with status information from other patients in the vicinity of said patient, said status information with data from scientific and medical publications, said status information with data manually inserted by the doctor and any combination thereof.

17. The method according to claim 1, wherein said (i)-(vi) are initiated at a time from 10 minutes to 8 hours prior to said at least one time of dispensing said at least one pharmaceutical.

18. The method according to claim 1, wherein said automatic pharmaceutical dispensing assessment unit is located outside said pharmaceutical dispensing machine.

19. The method according to claim 1, wherein said automatic pharmaceutical dispensing assessment unit is located at a remote location and in direct communication with said pharmaceutical dispensing machine.

20. The method according to claim 5, wherein said notifying said at least one physician of said at least one amended pharmaceutical dispensing regime further comprises requesting an approval from said at least one physician of said at least one amended pharmaceutical dispensing regime.

21. The automatic pharmaceutical dispensing assessment unit according to claim 9, wherein said (iv)-(ix) are initiated at a time from 10 minutes to 8 hours prior to said at least one time of dispensing said at least one pharmaceutical.

* * * * *